United States Patent
Inokuchi et al.

(10) Patent No.: US 12,036,306 B2
(45) Date of Patent: Jul. 16, 2024

(54) COSMETIC PRODUCT

(71) Applicant: SHIN-ETSU CHEMICAL CO., LTD., Tokyo (JP)

(72) Inventors: Yoshinori Inokuchi, Annaka (JP); Masayuki Konishi, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 577 days.

(21) Appl. No.: 17/291,903

(22) PCT Filed: Oct. 29, 2019

(86) PCT No.: PCT/JP2019/042319
§ 371 (c)(1),
(2) Date: May 6, 2021

(87) PCT Pub. No.: WO2020/095757
PCT Pub. Date: May 14, 2020

(65) Prior Publication Data
US 2022/0000756 A1  Jan. 6, 2022

(30) Foreign Application Priority Data
Nov. 7, 2018 (JP) ................................ 2018-209901

(51) Int. Cl.
| | | |
|---|---|---|
| *A61K 8/89* | (2006.01) | |
| *A61K 8/02* | (2006.01) | |
| *A61K 8/92* | (2006.01) | |
| *A61Q 17/04* | (2006.01) | |

(52) U.S. Cl.
CPC ................ *A61K 8/89* (2013.01); *A61K 8/025* (2013.01); *A61K 8/92* (2013.01); *A61Q 17/04* (2013.01); *A61K 2800/31* (2013.01); *A61K 2800/412* (2013.01); *A61K 2800/546* (2013.01)

(58) Field of Classification Search
None
See application file for complete search history.

(56) References Cited

U.S. PATENT DOCUMENTS

2019/0350835 A1    11/2019    Konishi

FOREIGN PATENT DOCUMENTS

| EP | 3 072 915 A1 | 9/2016 |
|---|---|---|
| JP | 2002-187811 A | 7/2002 |
| JP | 2002-241215 A | 8/2002 |
| JP | 2008-156254 A | 7/2008 |
| JP | 2009-132638 A | 6/2009 |
| JP | 2010-120914 A | 6/2010 |
| JP | 2014-91741 A | 5/2014 |
| JP | 2014-159550 A | 9/2014 |
| JP | 2014159550 A * | 9/2014 |
| JP | 2015-193564 A | 11/2015 |
| JP | 2017-193529 A | 10/2017 |
| WO | WO 2018/143061 A1 | 8/2018 |

OTHER PUBLICATIONS

English language translation of JP 2014 159550 A, Publ. Sep. 4, 2014. (Year: 2014).*
Extended European Search Report issued Aug. 9, 2022, in European Patent Application No. 19881856.9.
International Search Report issued in PCT/JP2019/042319 (PCT/ISA/210), dated Jan. 21, 2020.
Written Opinion of the International Searching Authority issued in PCT/JP2019/042319 (PCT/ISA/237), dated Jan. 21, 2020.

* cited by examiner

*Primary Examiner* — Dominic Lazaro
(74) *Attorney, Agent, or Firm* — Birch, Stewart, Kolasch & Birch, LLP

(57) ABSTRACT

This cosmetic product has extensibility and imparts use feels such as silkiness and smoothness, and further demonstrates excellent soft focus effects, and contains: (A) spherical organopolysiloxane particles of which 90% by mole or more are constituted from organosilsesquioxane units and which have a volume average particle size of 0.1 to 30 μm and an average refractive index of 1.44 to 1.57, and; (B) an oil agent; and one or more selected from (C) a silicone crosslinked product and (D) a silicon resin coating silicon rubber powder.

9 Claims, No Drawings

COSMETIC PRODUCT

TECHNICAL FIELD

The present invention relates to a cosmetic that contains spherical organopolysiloxane particles.

BACKGROUND ART

Spherical polymethylsilsesquioxane particles have hitherto been used in foundation and other makeup cosmetics for the purpose of giving a smooth, silky feel on use and for imparting extensibility. Polymethylsilsesquioxane particles can also impart a soft focus effect owing to their light-diffusing properties. The purpose of foundation and other makeup cosmetics is to conceal shape imperfections in the skin such as wrinkles, pores and coarse texture, as well as skin tone imperfections such as blemishes and freckles, and thus make the skin look smooth and beautiful. In recent years, emphasis has been placed on a finished look that appears natural and unadorned rather than artificial.

The natural finished look of a cosmetic is valued when the cosmetic is free of unnatural gloss (luster) and has a high transparency. Examples of known cosmetics that use polymethylsilsesquioxane particles include such art as facial shine-preventing preparations and preparations for correcting pores, wrinkles and the like (Patent Document 1: JP-A 2002-187811, Patent Document 2: JP-A 2002-241215). Yet, although such a pore or wrinkle-correcting effect can to some degree be imparted by polymethylsilsesquioxane particles, this has not been entirely satisfactory.

Also, spherical polymethylsilsesquioxanes are included in sunscreen cosmetics for the purpose of suppressing the stickiness of ultraviolet absorbers formulated therein (Patent Document 3: JP-A 2010-120914, Patent Document 4: JP-A 2014-91741). However, such polymethylsilsesquioxanes adversely affect the transparency, sometimes resulting in an unnatural finish.

PRIOR ART DOCUMENTS

Patent Documents

Patent Document 1: JP-A 2002-187811
Patent Document 2: JP-A 2002-241215
Patent Document 3: JP-A 2010-120914
Patent Document 4: JP-A 2014-91741

SUMMARY OF INVENTION

Technical Problem

In light of the above circumstances, the object of this invention is to provide spherical organopolysiloxane particle-containing cosmetics which have a feel on use that is silky and smooth, impart extensibility, and moreover exhibit an excellent soft focus effect.

Solution to Problem

The inventors have conducted extensive investigations in order to achieve this object, discovering as a result that by including spherical organopolysiloxane particles which are at least 90 mol % composed of organosilsesquioxane units and have a specific volume mean particle size and a specific average refractive index, including an oil and additionally formulating the cosmetic with one or more substance selected from crosslinked silicones and silicone resin-coated silicone rubber powders, the resulting cosmetic has a good feel on use and a good extensibility, the transparency of the cosmetic is maintained and the light diffusing properties can be increased. They have also discovered that by using organopolysiloxane particles having a specific average refractive index to adjust the refractive index of the oil, a cosmetic can be obtained which, in addition to a good feel on use and a good extensibility, manifests the desired effects. That is, the inventors have found that when the refractive index of the oil is set to a low value relative to the average refractive index of the spherical polyorganosilsesquioxane particles, a skin texture-correcting cosmetic which has a soft focus effect and a transparent look that are particularly outstanding can be obtained, and that when the refractive index of the oil is set to a value close to the average refractive index of the spherical polyorganosilsesquioxane particles, a sunscreen cosmetic which has a transparent look that is particularly outstanding can be obtained.

Accordingly, this invention provides the following cosmetic.

1. A cosmetic which includes:
   (A) spherical organopolysiloxane particles which are at least 90 mol % composed of organosilsesquioxane units and have a volume mean particle size of from 0.1 to 30 μm and an average refractive index of from 1.44 to 1.57,
   (B) an oil, and
   one, two or more substance selected from (C) crosslinked silicones and (D) silicone-resin-coated silicone rubber powders.
2. The cosmetic of 1 above, wherein the spherical organopolysiloxane particles of component (A) are spherical polymethylphenylsilsesquioxane particles consisting of units represented as $CH_3SiO_{3/2}$ and units represented as $C_6H_5SiO_{3/2}$, the molar ratio of $CH_3SiO_{3/2}$ units to $C_6H_5SiO_{3/2}$ units ($CH_3SiO_{3/2}$ units:$C_6H_5SiO_{3/2}$ units) being from 95:5 to 20:80.
3. The cosmetic of 2 above, wherein the molar ratio of $CH_3SiO_{3/2}$ units to $C_6H_5SiO_{3/2}$ units ($CH_3SiO_{3/2}$ units: $C_6H_5SiO_{3/2}$ units) is from 80:20 to 50:50.
4. The cosmetic of any of 1 to 3 above, wherein the spherical organopolysiloxane particles of component (A) have, as a dispersion obtained by dispersing 1 wt % of component (A) in a swollen, partially crosslinked methylpolysiloxane, a total light transmittance (JIS K 7361) and a haze (JIS K 7136) at a thickness of 500 μm which are each at least 80%.
5. The cosmetic of any of 1 to 4 above, wherein the total oil that is liquid at 25° C. within the cosmetic has a refractive index of at least 1.38 and less than 1.44, which cosmetic is a skin texture-correcting cosmetic.
6. The cosmetic of 5 above which is a nonaqueous composition.
7. The cosmetic of any of 1 to 4 above, wherein the total oil that is liquid at 25° C. within the cosmetic has a refractive index that is from 1.44 to 1.57, which cosmetic is a sunscreen cosmetic.
8. The cosmetic of 7 above which is a nonaqueous composition.

Advantageous Effects of Invention

The present invention enables cosmetics to be provided which impart both an excellent soft focus effect that renders indistinct primarily pores, wrinkles and other surface imperfections on the face and an excellent transparent look, have an outstanding feel on use that is silky and smooth, and have excellent extensibility and are thus easy to spread.

DESCRIPTION OF EMBODIMENTS

The invention is described in detail below.

[Component (A)]

Component (A) is spherical organopolysiloxane particles which are at least 90 mol % composed of organosilsesquioxane units and have a volume mean particle size of from 0.1 to 30 μm and an average refractive index of from 1.44 to 1.57. The organopolysiloxane particles (A) may be of one type used alone or two or more types may be suitably combined and used together.

To be able to obtain the rolling effect as a spherical powder from the organopolysiloxane particles (A), the volume mean particle size is from 0.1 to 30 μm, and preferably from 0.5 to 10 μm. When the volume mean particle size is less than 0.1 μm, the cosmetic is unlikely to exhibit a silky, smooth feel on use and good extensibility. The soft focus effect is also low. On the other hand, when the volume mean particle size exceeds 30 μm, the silky feel and smoothness of the cosmetic diminish, a gritty feel sometimes arises, and the soft focus effect is low.

The volume mean particle size (MV) is measured by such methods as microscopy, light scattering methods, laser diffraction methods, sedimentation in liquid methods and electrical sensing zone methods. For example, at a particle size of at least 0.1 μm but less than 1 μm, measurement by a light scattering method is desirable; at a particle size in the range of 1 to 30 μm, measurement by an electrical sensing zone method is desirable. In this Specification, "spherical" does not mean only true spheres, but encompasses also approximately spherical shapes. For example, it is meant to include also distorted ellipsoids in which the ratio of the length of the longest axis to the length of the shortest axis (aspect ratio) is on average generally in the range of from 1 to 4, preferably from 1 to 2, more preferably from 1 to 1.6, and even more preferably from 1 to 1.4. The particle shapes can be confirmed by examination with an optical microscope or an electron microscope. Regarding the particle size dispersity, the particle size may be monodisperse or polydisperse. Although structural color can sometimes be obtained when the particle size is monodisperse at 0.1 to 1 μm, in all of these cases, a sufficient soft focal effect can be obtained.

The organopolysiloxane particles (A) have an average refractive index of from 1.44 to 1.57, preferably from 1.47 to 1.52. At an average refractive index below 1.44 or above 1.57, the soft focus effect of the cosmetic decreases. The refractive index of the particles may be uniform or may not be uniform. That is, at the interior of the particles, the refractive index may be uniform or may be non-uniform. Or the refractive index may differ with the particle.

[Measurement of Average Refractive Index of Organopolysiloxane Particles]

Mixed solutions having refractive indices of 1.46, 1.47, 1.48, 1.49, 1.50, 1.51 and 1.52 are prepared using decamethylcyclopentasiloxane (refractive index, 1.40) and methylphenylpolysiloxane (refractive index, 1.53) and varying the blending ratio therebetween. Methylphenylpolysiloxane (refractive index, 1.53) is also prepared. Twenty grams of the respective prepared liquids is weighed into separate 25 mL glass vials and 1 g of powder is added to each, following which the vial is stoppered and the powder is uniformly dispersed in the liquid by 5 minutes of shaking. After 10 minutes at rest, the transparency is examined. The refractive index of the liquid having the highest transparency is taken to be the average refractive index of the powder.

The organopolysiloxane particles (A) are at least 90 mol %, preferably at least 95 mol %, composed of organosilsesquioxane units. The particles may even be 100 mol % composed of organosilsesquioxane units (polyorganosilsesquioxane particle). However, in addition to organosilsesquioxane units represented by the formula $R^1SiO_{3/2}$, one or more type of unit from among $R^1{}_2SiO_{2/2}$ units, $R^1{}_3SiO_{1/2}$ units and $SiO_{4/2}$ units may be included within a range that does not adversely affect properties such as the non-agglomeration and dispersibility of the particles.

Examples of organosilsesquioxane units include structural units represented by the general formula $R^1SiO_{3/2}$ (wherein $R^1$ is a monovalent organic group of 1 to 20 carbon atoms), the organopolysiloxane being a (co)polymer containing these. The organopolysiloxane may be a (co)polymer composed of two or more types of structural units having differing $R^1$ moieties.

$R^1$ is a monovalent organic group of from 1 to 20 carbon atoms. Examples of $R^1$ include alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups; cycloalkyl groups such as cyclobutyl, cyclopentyl, cyclohexyl and cycloheptyl groups; aryl groups such as phenyl, tolyl and naphthyl groups; aralkyl groups such as benzyl, phenethyl and β-phenylpropyl groups; alkenyl groups such as vinyl and allyl groups; and hydrocarbon groups in which some or all hydrogen atoms bonded to carbon atoms on the foregoing groups are substituted with atoms such as halogen atoms (fluorine atoms, chlorine atoms, bromine atoms, iodine atoms) and/or substituents such as acryloyloxy groups, methacryloyloxy groups, epoxy groups, glycidoxy groups, amino groups, mercapto groups and carboxyl groups. Of these, in terms of the ease of forming spherical particles and inertness, methyl and phenyl groups are preferred. That is, spherical polymethylphenylsilsesquioxane particles consisting of methylsilsesquioxane units represented as $CH_3SiO_{3/2}$ and phenylsilsesquioxane units represented as $C_6H_5SiO_{3/2}$ are preferred.

When component (A) is spherical polymethylphenylsilsesquioxane particles composed of units represented as $CH_3SiO_{3/2}$ and units represented as $C_6H_5SiO_{3/2}$, the molar ratio of $CH_3SiO_{3/2}$ units to $C_6H_5SiO_{3/2}$ units ($CH_3SiO_{3/2}$ units:$C_6H_5SiO_{3/2}$ units) is preferably from 95:5 to 20:80, and more preferably from 80:20 to 50:50. By varying this molar ratio within the range of 95:5 to 20:80, the average refractive index can be varied within the range of 1.44 to 1.57. In order to set the average refractive index to a value of from 1.47 to 1.52, the molar ratio of methylsilsesquioxane units to phenylsilsesquioxane units should be set within the range of 80:20 to 50:50.

The organopolysiloxane particles (A) preferably have, as a dispersion obtained by dispersing 1 wt % of component (A) in a swollen, partially crosslinked methylpolysiloxane, a total light transmittance (JIS K 7361) and a haze (JIS K 7136) which, when measured at a thickness of 500 μm, are each 80% or more. The total liquid transmittance and haze are each more preferably at least 85%, and even more preferably at least 90%.

When organopolysiloxane particles having a total liquid transmittance of at least 80% are used in cosmetics, a more transparent look that gives a natural finish is achieved, and when organopolysiloxane particles having a haze of at least 80% are used in cosmetics, a better soft focus effect is obtained. Hence, by having both be at least 80%, the desired effects of the invention can be better achieved.

The methods for measuring total light transmittance and haze are described.

A dispersion is prepared by dispersing 1 wt % of the sample in a swollen, partially crosslinked methylpolysiloxane, and measurement is carried out at a thickness of 500 μm. Measurement of the total light transmittance is based on JIS K 7361, and measurement of the haze is based on JIS K 7136. As used herein, "swollen, partially crosslinked methylpolysiloxane" refers to a gel obtained by swelling from 20 to 30 wt % of a partially crosslinked methylpolysiloxane with 6 mm$^2$/s methylpolysiloxane and having a refractive index of from 1.39 to 1.41; it has a total liquid transmittance of at least 90% and a haze of less than 10%. An example of a commercial product is KSG-16 from Shin-Etsu Chemical Co., Ltd. (total light transmittance, 93.2%; haze, 6.8%).

In one specific method for preparing the measurement samples, a three-roll mill is used to disperse component (A) to a concentration of 1 wt % in swollen, partially crosslinked methylpolysiloxane, and measurement is carried out at a dispersion thickness of 500 μm on a 1 mm thick quartz glass plate. The measurement apparatus used may be, for example, the HR-100 Haze Meter from the Murakami Color Research Laboratory. Total light transmittance is measured in accordance with JIS K 7361, and haze is measured in accordance with JIS K 7136. When measuring the swollen, partially crosslinked methylpolysiloxane, aside from not dispersing the powder, the same conditions are used at the time of measurement.

The organopolysiloxane particles (A) can be produced by a known method. For example, first one or more type of organotrialkoxysilane of the general formula $R^1Si(OR^2)_3$ (wherein $R^1$ is a monovalent organic group of 1 to 20 carbon atoms and $R^2$ is an unsubstituted monovalent hydrocarbon group of 1 to 6 carbon atoms) is added to an aqueous solution of an alkaline substance to effect hydrolysis and condensation reactions, thereby giving an aqueous dispersion. Alternatively, one or more type of organotrialkoxysilane is added to an aqueous solution of an acidic substance to effect hydrolysis, and an alkaline substance is added thereto, thereby effecting a condensation reaction and obtaining an aqueous dispersion. Next, water and by-product alcohol are removed from the resulting aqueous dispersion by drying under applied heat. As a result, spherical organopolysiloxane particles (polyorganosilsesquioxane particles) can be obtained. In cases where the resulting particles have agglomerated, the agglomerates are broken down on a grinding mill.

The organopolysiloxane particles (A) can be used in various applications, and are especially suitable as an ingredient for all cosmetics used externally on the skin or hair. The amount in which the organopolysiloxane particles (A) are included is not particularly limited, although the content is preferably from 0.1 to 40 wt %, and more preferably from 0.1 to 20 wt %, of the overall cosmetic. To achieve a satisfactory skin texture-correcting effect, the content is preferably at least 0.1 wt %; to achieve a transparent look, the content is preferably not more than 40 wt %.

[Component (B)]

Component (B) of the invention is an oil. One type of oil may be used alone or two or more may be used in suitable combination. The oil may be solid, semi-solid or liquid at room temperature. Examples include silicone oils, natural animal and plant oils and fats, semi-synthetic oils and fats, hydrocarbon oils, waxes, higher alcohols, fatty acids, ester oils, fluorocarbon oils and ultraviolet absorbers. The organopolysiloxane particles (A) of the invention have an excellent dispersibility in the oil (B).

Silicone Oils

The silicone oils are not particularly limited, provided that they are ingredients which can generally be included in cosmetics. Examples include low-viscosity to high-viscosity, linear or branched organopolysiloxanes such as dimethylpolysiloxane, decamethylcyclopentasiloxane, dodecamethylcyclohexasiloxane, disiloxane, trisiloxane, methyl trimethicone, caprylyl methicone, methyl phenyl polysiloxane, methyl hexyl polysiloxane, methyl hydrogen polysiloxane and dimethylsiloxane-methyl phenyl siloxane copolymers; and amino-modified organopolysiloxanes. Of these, volatile silicones that enable a light feel on use to be obtained, low-viscosity silicones (including commercial products available from Shin-Etsu Chemical Co., Ltd., such as TMF-1.5, KF-995, KF-96A-2cs and KF-96A-6cs), and phenyl silicones used for increasing compatibility with other oils or for luster (including commercial products available from Shin-Etsu Chemical Co., Ltd., such as KF-56A and 54HV) are preferably used. One or more of these silicone oils may be used.

Natural Animal and Plant Oils and Fats, and Semi-Synthetic Oils and Fats

Examples of natural plant and animal fats and oils and semi-synthetic fats and oils include avocado oil, linseed oil, almond oil, Chinese wax, perilla oil, olive oil, cocoa butter, kaya oil, cod liver oil, beef tallow, neatsfoot oil, beef bone fat, hydrogenated beef tallow, apricot kernel oil, hydrogenated oil, wheat germ oil, sesame oil, rice germ oil, rice bran oil, camellia kissi oil, safflower oil, shea butter, Chinese paulownia oil, cinnamon oil, turtle oil, soybean oil, tea oil, camellia japonica seed oil, evening primrose oil, corn oil, lard, rapeseed oil, Japanese paulownia oil, germ oil, horse fat, persic oil, palm oil, palm kernel oil, castor oil, hydrogenated castor oil, castor oil fatty acid methyl ester, sunflower oil, grapeseed oil, jojoba oil, macadamia nut oil, mink oil, meadowfoam seed oil, cottonseed oil, coconut oil, hydrogenated coconut oil, glyceryl tricocoate, mutton tallow, peanut oil, lanolin, liquid lanolin, reduced lanolin, lanolin alcohol, hydrogenated lanolin, acetylated lanolin, acetylated lanolin alcohol, isopropyl lanolate, POE lanolin alcohol ethers, POE lanolin alcohol acetates, polyethylene glycol lanolate, POE hydrogenated lanolin alcohol ethers and egg yolk oil. Here, "POE" stands for polyoxyethylene.

Hydrocarbon Oils

Hydrocarbon oils are exemplified by linear, branched, and volatile hydrocarbon oils. Specific examples include hydrogenated polydecene, hydrogenated polybutene, liquid paraffin, light isoparaffin, isododecane, isohexadecane, light liquid isoparaffin, squalane, synthetic squalane, vegetable squalane, squalene and $C_{13-15}$ alkanes.

Waxes

Waxes that may be used in this invention are not particularly limited, provided that they are ingredients which can generally be included in cosmetics. Examples include hydrocarbon waxes such as ceresin, ozokerite, paraffin, synthetic waxes, microcrystalline wax and polyethylene wax; vegetable waxes such as carnauba wax, rice wax, rice bran wax, jojoba wax (including extremely hydrogenated jojoba oil) and candelilla wax; and animal waxes such as spermaceti, beeswax and Snow White Wax. In particular, silicone waxes (including commercial products available from Shin-Etsu Chemical Co., Ltd., such as KP-561P, 562P and KF-7020S) are preferably used for luster or to adjust the feeling on use.

Higher Alcohols

Higher alcohols are exemplified by alcohols having from 12 to 22 carbon atoms. Examples include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecynol, cholesterol, phytosterol, POE cholesterol ether, monostearyl glycerol ether (batyl alcohol) and monooleyl glyceryl ether (selachyl alcohol).

Fatty Acids

Examples of fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Ester Oils

Examples of ester oils include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol diheptanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, ethylhexyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, isopropyl lauroyl sarcosinate, diisostearyl malate, triethylhexanoin, $C_{12-15}$ alkyl benzoates, glyceryl tri(caprylate/caprate), cocoalkyl (caprylate/caprate), isodecyl neopentanoate, hexyl laurate, dicaprylyl carbonate, diisostearyl malate and diisopropyl adipate.

Fluorocarbon Oils (Excluding the Above Silicone Waxes)

Examples of fluorocarbon oils include perfluoropolyether, perfluorodecalin and perfluorooctane.

Ultraviolet Absorbers

Examples of ultraviolet absorbers include homomenthyl salicylate, octocrylene, 4-tert-butyl-4'-methoxydibenzoyl-methane, 4-(2-β-glucopyranosiloxy)propoxy-2-hydroxy-benzophenone, octyl salicylate, hexyl 2-[4-(diethylamino)-2-hydroxybenzoyl] benzoate, dihydroxydimethoxybenzophenone, dihydroxydimethoxybenzophenonedisulfonic acid sodium salt, dihydroxybenzophenone, dimethicodiethylbenzal malonate, 1-(3,4-dimethoxyphenyl)-4,4-dimethyl-1,3-pentanedione, 2-ethylhexyl dimethoxybenzylidene dioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methylbis(trimethylsiloxy)silylisopentyl trimethoxycinnamate, drometrizole trisiloxane, 2-ethylhexyl p-dimethylaminobenzoate, isopropyl p-methoxycinnamate, 2-ethylhexyl p-methoxycinnamate, 2,4-bis-[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenonesulfonic acid and the trihydrate thereof, sodium hydroxymethoxybenzophenonesulfonate, phenylbenzimidazolesulfonic acid and 2,2'-methylenebis(6-(2H-benzotriazol-2-yl)-4-(1,1,3,3-tetramethylbutyl)phenol. Also, a UVA absorber (e.g., hexyl diethylaminohydroxybenzoyl benzoate) and a UVB absorber (e.g., ethylhexyl methoxycinnamate) may be used together, with optional combinations of each also being possible.

When the oil (B) has a suitable refractive index, a high light scattering ability and transparency can be obtained in the cosmetic of the invention. Particularly in the case of skin texture-correcting cosmetics such as concealers, the refractive index of the overall oil that is liquid at 25° C. in the cosmetic is preferably at least 1.38 but less than 1.44, more preferably from 1.38 to 1.42, and even more preferably from 1.39 to 1.41. Examples of low-refractive-index oils include volatile silicones, non-volatile dimethylpolysiloxanes, and low-molecular-weight ester oils. In particular, preferred use can be made of cyclopentasiloxane (refractive index, 1.396), methyl trimethicone (refractive index, 1.386) and dimethicone (refractive index, 1.387 to 1.403), as defined in the International Nomenclature of Cosmetic Ingredients (INCI).

When the oil has a suitable refractive index, a high light transmittance can be obtained in the cosmetic of the invention. Particularly in the case of sunscreen cosmetics formulated with an ultraviolet absorber, the refractive index of the overall oil that is liquid at 25° C. in the cosmetic is preferably from 1.44 to 1.57, more preferably from 1.44 to 1.52, and even more preferably from 1.45 to 1.50. Examples of high refractive index oils include ultraviolet absorbers and phenyl silicones. In particular, preferred use can be made of ethylhexyl methoxycinnamate (refractive index, 1.543), ethylhexyl salicylate (refractive index, 1.502), homosalate (refractive index, 1.517), octocrylene (refractive index, 1.567) and diphenylsiloxy phenyl trimethicone (refractive index, 1.498), as defined in the International Nomenclature of Cosmetic Ingredients (INCI). In addition, component (A) of the invention exhibits a high dispersibility with ultraviolet absorbers, and so a good feeling on use can be obtained.

The content of the oil (B), although not particularly limited, is preferably from 1 to 95 wt %, and more preferably from 15 to 40 wt %, of the overall cosmetic. The content of oil that is liquid at 25° C. is preferably from 1 to 90 wt %, and more preferably from 15 to 40 wt %, of the overall cosmetic. Of the overall oil content, silicone oils account for preferably at least 5 wt %, more preferably at least 20 wt %, and even more preferably at least 35 wt %. There is no particular upper limit, although this may be set to 95 wt % or less.

The cosmetic of the invention includes one, two or more substances selected from (C) crosslinked silicones and (D) silicone resin-coated silicone rubber powders.

[Component (C)]

Component (C) in the invention is crosslinked silicone. One type may be used alone or two or more may be used in suitable combination. Exemplary crosslinked silicones include partially crosslinked methyl polysiloxanes, partially crosslinked polyether-modified silicones and partially crosslinked polyglycerol-modified silicones. One type may be used alone or two or more may be used in suitable combination. Specific examples include the following from Shin-Etsu Chemical Co., Ltd.: KSG-210, 240, 310, 320, 330, 340, 320Z, 350Z, 710, 810, 820, 830, 840, 820Z and 850Z. In particular, elastomers which are compounds without polyether or polyglycerol structures on the molecule and which, by swelling the oil, have a structural viscosity are preferred. Specific examples include (dimethicone/vinyl dimethicone) crosspolymer, (dimethicone/phenyl vinyl dimethicone) crosspolymer, (vinyl dimethicone/lauryl dimethicone) crosspolymer and (lauryl polydimethylsiloxyethyl dimethicone/bis-vinyl dimethicone) crosspolymer, as defined in the International Nomenclature of Cosmetic Ingredients (INCI). These are commercially available as swollen products which contain oil that is liquid at room temperature; specific examples include the following from Shin-Etsu Chemical Co., Ltd.: KSG-15, 1510, 16, 1610, 18A, 19, 41A, 42A, 43, 44, 042Z, 045Z and 048Z.

The content of component (C) is not particularly limited, although the content as solids is preferably from 0.1 to 25 wt %, more preferably from 0.2 to 20 wt %, and even more preferably from 0.5 to 15 wt %, of the overall cosmetic. For a sufficient skin texture-correcting effect, a content of at least 0.1 wt % is preferred. On the other hand, at more than 25 wt %, the feel to the touch may become heavy.

[Component (D)]

Component (D) of the invention is a silicone resin-coated silicone rubber powder. One type may be used alone or two or more may be used in suitable combination. It is preferable to include component (D) on account of its stickiness prevention and other tactile feel-improving effects and its wrinkle, pore and other skin texture-correcting effects. Specific examples of silicone resin-coated silicone rubber powders include those known by such names as (vinyl dimethicone/methicone silsesquioxane) crosspolymer, (diphenyl dimethicone/vinyl diphenyl dimethicone/silsesquioxane) crosspolymer, polysilicone-22 and polysilicone-1 crosspolymer, as defined in the International Nomenclature of Cosmetic Ingredients (INCI). These are commercially available under trade names such as KSP-100, 101, 102, 105, 300, 411 and 441 (Shin-Etsu Chemical Co., Ltd.)

When component (D) is included, the content is preferably from 0.1 to 25 wt %, more preferably from 0.5 to 20 wt %, and even more preferably from 1.0 to 18 wt %, of the overall cosmetic. A content of at least 0.1 wt % is preferred from the standpoint of the tactile feel-improving effects; a content of not more than 25 wt % is preferred from the standpoint of the transparent look.

[Other Ingredients]

Various ingredients used in conventional cosmetics may be included as other ingredients in the cosmetic of the invention. Such other ingredients are exemplified by (E) powders other than components (A) and (D), (F) surfactants, (G) film-forming agents, (H) aqueous ingredients and (I) other additives. These may be used singly or two or more may be used in suitable combination. These ingredients are suitably selected and used according to considerations such as the type of cosmetic. The contents thereof also may be set to known contents according to, for example, the type of cosmetic.

(E) Powders Other than Components (A) and (D)

Powders other than components (A) and (D) are not particularly limited, provided that they are ingredients which can be included in conventional cosmetics. Examples include pigments and spherical silicone powders. When such powders are included, the content thereof is not particularly limited, although it is preferable to include the powders in an amount of from 0.1 to 90%, and more preferably from 1 to 35%, of the overall cosmetic. Examples of powders other than components (A) and (D) include the following.

Spherical Silicone Powders

Spherical silicone powders are exemplified by crosslinked silicone powders (i.e., so-called silicone rubber powders composed of organopolysiloxane having a structure in which repeating chains of diorganosiloxane units are crosslinked) and silicone resin particles other than components (A) and (D) (polyorganosilsesquioxane resin particles having a three-dimensional network structure). Specific examples are known by names such as (dimethicone/vinyl dimethicone) crosspolymer and polymethylsilsesquioxane. These are commercially available as powders or as silicone oil-containing swollen products, examples of which include the products sold under the trade names KMP-598, 590, 591 and KSG-016F (all from Shin-Etsu Chemical Co., Ltd.).

Pigments

The pigments are not particularly limited, provided that they can generally be used in makeup cosmetics. Examples include inorganic pigments such as talc, mica, sericite, synthetic fluorphlogopite, barium sulfate, aluminum oxide, kaolin, silica, calcium carbonate, zinc oxide, titanium oxide, red iron oxide, yellow iron oxide, black iron oxide, ultramarine, Prussian blue, carbon black, titanium suboxide, cobalt violet, chromium oxide, chromium hydroxide, cobalt titanate, bismuth oxychloride and titanium-mica pearlescent pigments; organic pigments such as zirconium, barium or aluminum lakes of Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404 and Green No. 3; natural colorants such as chlorophyll and β-carotene; and dyes.

The above-mentioned powders may also be used in a form in which the particles have been surface-treated. The surface treatment agent is preferably one that can impart hydrophobicity so that the water resistance of the preparation is not lost, and is not particularly limited provided that hydrophobicity can be imparted. Exemplary surface treatment agents include silicone treatment agents, waxes, paraffins, organofluorine compounds such as perfluoroalkyl phosphates, surfactants, amino acids such as N-acylglutamic acid, and metal soaps such as aluminum stearate and magnesium myristate. More preferred silicone treatment agents include silanes or silylating agents such as caprylylsilane (AES-3083, from Shin-Etsu Chemical Co., Ltd.) and trimethoxysilyl dimethicone; silicone oils such as dimethylsilicone (KF-96A Series, from Shin-Etsu Chemical Co., Ltd.), methylhydrogen-type polysiloxanes (e.g., KF-99P and KF-9901, from Shin-Etsu Chemical Co., Ltd.) and silicone-branched silicone treatment agents (e.g., KF-9908 and KF-9909, from Shin-Etsu Chemical Co., Ltd.); and silicone acrylates (KP-574, KP-541, from Shin-Etsu Chemical Co., Ltd.). In addition, the surface hydrophobizing treatment agent may be of one type used alone or two or more may be used in combination. Specific examples of surface-treated coloring pigments include the KTP-09 series from Shin-Etsu Chemical Co., Ltd., especially KTP-09W, 09R, 09Y and 09B. Specific examples of dispersions that contain hydrophobized microparticulate titanium oxide or hydrophobized microparticulate zinc oxide include SPD-T5, T6, T7, TSL, Z5, Z6 and Z5L, all from Shin-Etsu Chemical Co., Ltd. When these ingredients are included, the content thereof within the cosmetic is preferably from 0.01 to 95 wt %.

(F) Surfactants

The surfactants are exemplified by nonionic, anionic, cationic and amphoteric surfactants, and are not particularly limited. Use can be made of any surfactant used in conventional cosmetics. One surfactant may be used alone or two or more may be used in suitable combination. Of these surfactants, linear or branched polyoxyethylene-modified organopolysiloxanes, linear or branched polyoxyethylene-polyoxypropylene-modified organopolysiloxanes, linear or branched polyoxyethylene/alkyl co-modified organopolysiloxanes, linear or branched polyoxyethylene-polyoxypropylene/alkyl co-modified organopolysiloxanes, linear or branched polyglycerol-modified organopolysiloxanes and linear or branched polyglycerol/alkyl co-modified organopolysiloxanes are preferred. In these surfactants, the content of hydrophilic polyoxyethylene groups, polyoxyethylene-polyoxypropylene groups or polyglycerol residues preferably accounts for 10 to 70% of the molecule. Specific examples include the following from Shi-Etsu Chemical Co., Ltd.: KF-6011, 6013, 6017, 6043, 6028, 6038, 6048, 6100, 6104, 6105 and 6106. When a surfactant is included, the content thereof is preferably from 0.01 to 15% of the cosmetic.

(G) Film-Forming Agents

The film-forming agents are not particularly limited, provided that they are ingredients which can be included in conventional cosmetics. Specific examples include latexes of polyvinyl alcohol, polyvinyl pyrrolidone, polyvinyl acetate, polyalkyl acrylate, etc.; cellulose derivatives such as dextrin, alkyl cellulose and nitrocellulose; siliconized polysaccharide compounds such as tri(trimethylsiloxy)silylpropylcarbamoyl pullulan, acrylate-silicone graft copolymers such as (alkyl acrylate/dimethicone) copolymers, silicone resins such as trimethylsiloxysilicate, silicone-modified polynorbornene, silicone-based resins such as fluorine-modified silicone resins, fluorocarbon resins, aromatic hydrocarbon resins, polymer emulsion resins, terpene resins, polybutenes, polyisoprenes, alkyd resins, polyvinyl pyrrolidone-modified polymers, rosin-modified resins and polyurethanes.

Of these, silicone-based film-forming agents are especially preferred. Examples include, but are not limited to, tri(trimethylsiloxy)silylpropylcarbamic acid pullulan (commercially available in solvent-dissolved forms as TSPL-30-D5 and ID from Shin-Etsu Chemical Co., Ltd.), (alkyl acrylate/dimethicone) copolymers (available in solvent-dissolved forms as KP-543, 545, 549, 550 and 545L from Shin-Etsu Chemical Co., Ltd.), trimethylsiloxysilicate (available in solvent-dissolved forms as KF-7312J and X-21-5250 from Shin-Etsu Chemical Co., Ltd.), silicone-modified polynorbornene (available in a solvent-dissolved form as NBN-30-ID from Shin-Etsu Chemical Co., Ltd.) and organosiloxane graft polyvinyl alcohol-based polymers. When a film-forming agent is included, the content thereof is preferably from 0.1 to 20% of the cosmetic.

(H) Aqueous Ingredients

The aqueous ingredients are not particularly limited, provided that they are aqueous ingredients which can be included in conventional cosmetics. Exemplary aqueous ingredients include water and humectants such as lower alcohols, sugar alcohols and polyhydric alcohols. One aqueous ingredient may be used alone or two or more may be used in suitable combination. When an aqueous ingredient is included, the content thereof within the cosmetic preparation is preferably from 0.1 to 90%.

(I) Other Additives

Examples of other additives include oil-soluble gelling agents, antiperspirants, preservatives and bactericides, fragrances, salts, antioxidants, pH adjustors, chelating agents, algefacients, anti-inflammatory agents and skin beautifying ingredients (whitening agents, cell activators, skin roughness improvers, circulation promoting ingredients, skin astringents, antiseborrheic agents, etc.), vitamins, amino acids, water-soluble polymeric compounds, fibers and inclusion compounds.

Oil-Soluble Gelling Agents

Examples of oil-soluble gelling agents include metal soaps such as aluminum stearate, magnesium stearate and zinc myristate; amino acid derivatives such as bis-ethylhexyl bis-oleyl pyromellitamide, dibutyl ethylhexanoyl glutamide, dibutyl lauroyl glutamide, N-lauroyl-L-glutamic acid and α,γ-di-n-butylamine; dextrin fatty acid esters such as dextrin palmitate, dextrin stearate and dextrin 2-ethylhexanoate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organic-modified clay minerals such as disteardimonium hectorite, stearalkonium hectorite and hectorite.

[Cosmetic]

The method of preparing the cosmetic of the invention is not particularly limited and involves mixing together the ingredients. Various methods may be used to include the organopolysiloxane particles (A) in the cosmetic. For example, the particles may be dispersed beforehand in the oil and rendered into a paste, they may be included in an aqueous phase by working them into a high-HLB activator, or they may be rendered into an oil-in-water emulsion and then formulated in the cosmetic.

The cosmetic may be in the form of an emulsion or a nonaqueous system. When the desire is to impart a fresh feel on use, an emulsified form is selected. The emulsified form may be any of the following: an oil-in-water (O/W) emulsion, water-in-oil (W/O) emulsion, oil-in-water-in-oil (O/W/O) emulsion or water-in-oil-in-water (W/O/W) emulsion. When the desire is to obtain an oily feel or water resistance, a nonaqueous composition or a powder composition can be selected. A good cosmetic can be obtained in either case. In particular, when the aim is to obtain a good skin texture-correcting effect in a skin texture-correcting cosmetic or to obtain a good water resistance in a sunscreen cosmetic, a nonaqueous composition is preferably selected. In this invention, "nonaqueous composition" refers to a composition in which water is intentionally not included, but also encompasses cases in which a trace amount of water is carried in by the ingredients.

The cosmetic of the invention is not particularly limited, so long as it is a cosmetic which includes the essential ingredients. It may be used in a variety of products, including beauty essences, milky lotions, creams, hair care products, foundations, makeup bases, sunscreens, concealers, cheek color, lipsticks, gloss, balms, mascaras, eye shadows, eye liners, body makeup, deodorants and nail cosmetics. Skin texture-correcting cosmetics which confer a skin texture-correcting effect and sunscreen cosmetics which impart a sunscreening effect to the above are especially preferred. The physical form of the inventive cosmetic may be selected from among various forms, including liquids, creams, solids, pastes, gels, mousses, sprays, clays, powders and sticks.

EXAMPLES

The invention is illustrated more fully below by way of Examples and Comparative Examples, although the invention is not limited by these Examples. Some of the ingredient names appearing below are from the International Nomenclature of Cosmetic Ingredients (INCI).

The measurement methods used in the Preparation Examples are described.

[Method of Measuring Average Refractive Index of Polyorganosilsesquioxane Particles]

Mixed solutions having refractive indices of 1.46, 1.47, 1.48, 1.49, 1.50, 1.51 and 1.52 were prepared using decamethylcyclopentasiloxane (refractive index, 1.40) and methylphenylpolysiloxane (refractive index, 1.53) and varying the blending ratio therebetween. Methylphenylpolysiloxane (refractive index, 1.53) was also prepared. Twenty grams of the respective prepared liquids was weighed into separate 25 mL glass vials and 1 g of powder was added to each, following which the vial was stoppered and the powder was uniformly dispersed in the liquid by 5 minutes of shaking. After 10 minutes at rest, the transparency was examined. The refractive index of the liquid having the highest transparency was taken to be the average refractive index of the powder.

[Method of Measuring Total Light Transmittance and Haze of Organopolysiloxane Particles (A)]

A three-roll mill was used to disperse the organopolysiloxane particles (A) to a concentration of 1 wt % in swollen, partially crosslinked methylpolysiloxane (KSG-16 from Shin-Etsu Chemical Co., Ltd. (total light transmittance, 93.2%; haze, 6.8%)), and the measurements were carried out at a dispersion thickness of 500 μm on a 1 mm thick quartz glass plate. The measurement apparatus was the HR-100 Haze Meter from the Murakami Color Research Laboratory. The total light transmittance was measured in accordance with JIS K 7361, and the haze was measured in accordance with JIS K 7136.

Preparation Example 1

A one-liter glass flask was charged with 801 g of deionized water and the water temperature was set to 20° C. The pH of the deionized water was measured and found to be 5.9. Next, 95.5 g of methyltrimethoxysilane was added under stirring with an anchor stirring element at a stirring speed of 150 rpm, whereupon heat generation occurred and the temperature rose to 24° C. The mixture assumed a clear state after 3 minutes and stirring was continued for another 7 minutes. Next, 62.5 g of phenyltrimethoxysilane was added and stirring was continued while keeping the temperature at 20 to 25° C., whereupon the mixture assumed a clear state after 50 minutes and stirring was continued for another 5 minutes. The mixture was then cooled to 5° C. over a period of 25 minutes. A mixed solution of 0.53 g of 28 wt % ammonia water and 2.65 g of deionized water was then poured in and the system was stirred for 30 seconds, following which stirring was stopped. Clouding arose 12 seconds after stirring was stopped.

The system was left at rest for 3 hours, following which stirring at a speed of 150 rpm was begun. The system was heated to 75° C. and 38 g of 28 wt % ammonia water was added, following which one hour of additional stirring was carried out at a temperature of 73 to 77° C. The system was then cooled to 30° C. or below, following which the liquid was removed using a press filter, leaving a filter cake. The cake was dried at a temperature of 105° C. in a circulating hot-air dryer, and the dried material was pulverized in a jet mill, giving polymethylphenylsilsesquioxane particles.

Based on the amounts of methyltrimethoxysilane and phenyltrimethoxysilane used as the starting materials, the molar ratio of methylsilsesquioxane units and phenylsilsesquioxane units in the resulting polymethylphenylsilsesquioxane particles was calculated to be 69:31.

The shapes of these polymethylphenylsilsesquioxane particles were examined under an electron microscope and found to be spherical. The volume mean size of the polymethylphenylsilsesquioxane particles was measured using an electrical sensing zone method particle size analyzer (Multisizer 3, from Beckman Coulter KK), and found to be 2.1 μm. The average refractive index, as measured by the method described above, was 1.49. The polymethylphenylsilsesquioxane particles were then dispersed to a concentration of 1 wt % in swollen, partially crosslinked methylpolysiloxane (KSG-16, from Shin-Etsu Chemical Co., Ltd.). Upon carrying out measurement under the conditions described above at a thickness of 500 μm, the total light transmittance was 91.8% and the haze was 90.6%.

Preparation Example 2

A one-liter glass flask was charged with 815 g of deionized water and the water temperature was set to 20° C. The pH of the deionized water was measured and found to be 5.9. Next, 77.6 g of methyltrimethoxysilane was added under stirring with an anchor stirring element at a stirring speed of 150 rpm, whereupon heat generation occurred and the temperature rose to 24° C. The mixture assumed a clear state after 3 minutes and stirring was continued for another 7 minutes. Next, 66.4 g of phenyltrimethoxysilane was added and stirring was continued while keeping the temperature at 20 to 25° C., whereupon the mixture assumed a clear state after 55 minutes and stirring was continued for another 5 minutes. The mixture was then cooled to 5° C. over a period of 25 minutes. A mixed solution of 0.54 g of 28 wt % ammonia water and 2.7 g of deionized water was then poured in and the system was stirred for 20 seconds, following which stirring was stopped. Clouding arose 12 seconds after stirring was stopped.

The system was left at rest for 3 hours, following which stirring at a speed of 150 rpm was begun. The system was heated to 75° C. and 38 g of 28 wt % ammonia water was added, following which one hour of additional stirring was carried out at a temperature of 73 to 77° C. The system was then cooled to 30° C. or below, following which the liquid was removed using a press filter, leaving a filter cake. The cake was dried at a temperature of 105° C. in a circulating hot-air dryer, and the dried material was pulverized in a jet mill, giving polymethylphenylsilsesquioxane particles.

Based on the amounts of methyltrimethoxysilane and phenyltrimethoxysilane used as the starting materials, the molar ratio of methylsilsesquioxane units and phenylsilsesquioxane units in the resulting polymethylphenylsilsesquioxane particles was calculated to be 63:37.

The shapes of these polymethylphenylsilsesquioxane particles were examined under an electron microscope and found to be spherical. The volume mean size of the polymethylphenylsilsesquioxane particles was measured using an electrical sensing zone method particle size analyzer (Multisizer 3, from Beckman Coulter KK), and found to be 2.1 μm. The average refractive index, as measured by the method described above, was 1.50. The polymethylphenylsilsesquioxane particles were then dispersed to a concentration of 1 wt % in swollen, partially crosslinked methylpolysiloxane (KSG-16, from Shin-Etsu Chemical Co., Ltd.). Upon carrying out measurement under the conditions described above at a thickness of 500 μm, the total light transmittance was 91.3% and the haze was 93%.

Preparation Example 3

A one-liter glass flask was charged with 789 g of deionized water and the water temperature was set to 20° C. The pH of the deionized water was measured and found to be 5.8. Next, 110.5 g of methyltrimethoxysilane was added under stirring with an anchor stirring element at a stirring speed of 150 rpm, whereupon heat generation occurred and the temperature rose to 24° C. The mixture assumed a clear state after 4 minutes and stirring was continued for another 6 minutes. Next, 59.5 g of phenyltrimethoxysilane was added and stirring was continued while keeping the temperature at 20 to 25° C., whereupon the mixture assumed a clear state after 45 minutes and stirring was continued for another 5 minutes. The mixture was then cooled to 5° C. over a period of 25 minutes. A mixed solution of 0.52 g of 28 wt % ammonia water and 2.6 g of deionized water was then poured in and the system was stirred for 30 seconds, following which stirring was stopped. Clouding arose 30 seconds after stirring was stopped.

The system was left at rest for 3 hours, following which stirring at a speed of 150 rpm was begun. The system was heated to 75° C. and 38 g of 28 wt % ammonia water was added, following which one hour of additional stirring was carried out at a temperature of 73 to 77° C. The system was then cooled to 30° C. or below, following which the liquid was removed using a press filter, leaving a filter cake. The cake was dried at a temperature of 105° C. in a circulating hot-air dryer, and the dried material was pulverized in a jet mill, giving polymethylphenylsilsesquioxane particles.

Based on the amounts of methyltrimethoxysilane and phenyltrimethoxysilane used as the starting materials, the molar ratio of methylsilsesquioxane units and phenylsilsesquioxane units in the resulting polymethylphenylsilsesquioxane particles was calculated to be 73:27.

The shapes of these polymethylphenylsilsesquioxane particles were examined under an electron microscope and found to be spherical. The volume mean size of the polymethylphenylsilsesquioxane particles was measured using an electrical sensing zone method particle size analyzer (Multisizer 3, from Beckman Coulter KK), and found to be 2.2 μm. The average refractive index, as measured by the method described above, was 1.48. The polymethylphenylsilsesquioxane particles were then dispersed to a concentration of 1 wt % in swollen partially crosslinked methylpolysiloxane (KSG-16, from Shin-Etsu Chemical Co., Ltd.). Upon carrying out measurement under the conditions described above at a thickness of 500 μm, the total light transmittance was 92.2% and the haze was 86.8%.

Preparation Example 4

A one-liter glass flask was charged with 754 g of deionized water and the water temperature was set to 20° C. The pH of the deionized water was measured and found to be 5.9. Next, 142.9 g of methyltrimethoxysilane was added under stirring with an anchor stirring element at a stirring speed of 150 rpm, whereupon heat generation occurred and the temperature rose to 24° C. The mixture assumed a clear state after 7 minutes and stirring was continued for another 8 minutes. Next, 62.1 g of phenyltrimethoxysilane was added and stirring was continued while keeping the temperature at 20 to 25° C., whereupon the mixture assumed a clear state after 35 minutes and stirring was continued for another 5 minutes. The mixture was then cooled to 5° C. over a period of 25 minutes. A mixed solution of 0.50 g of 28 wt % ammonia water and 2.5 g of deionized water was then poured in and the system was stirred for 30 seconds, following which stirring was stopped. Clouding arose 1 minute and 15 seconds after stirring was stopped.

The system was left at rest for 3 hours, following which stirring at a speed of 150 rpm was begun. The system was heated to 75° C. and 38 g of 28 wt % ammonia water was added, following which one hour of additional stirring was carried out at a temperature of 73 to 77° C. The system was then cooled to 30° C. or below, following which the liquid was removed using a press filter, leaving a filter cake. The cake was dried at a temperature of 105° C. in a circulating hot-air dryer, and the dried material was pulverized in a jet mill, giving polymethylphenylsilsesquioxane particles.

Based on the amounts of methyltrimethoxysilane and phenyltrimethoxysilane used as the starting materials, the molar ratio of methylsilsesquioxane units and phenylsilsesquioxane units in the resulting polymethylphenylsilsesquioxane particles was calculated to be 77:23.

The shapes of these polymethylphenylsilsesquioxane particles were examined under an electron microscope and found to be spherical. The volume mean size of the polymethylphenylsilsesquioxane particles was measured using an electrical sensing zone method particle size analyzer (Multisizer 3, from Beckman Coulter KK), and found to be 2.8 μm. The average refractive index, as measured by the method described above, was 1.47. The polymethylphenylsilsesquioxane particles were then dispersed to a concentration of 1 wt % in swollen partially crosslinked methylpolysiloxane (KSG-16, from Shin-Etsu Chemical Co., Ltd.). Upon carrying out measurement under the conditions described above at a thickness of 500 μm, the total light transmittance was 92.3% and the haze was 83.4%.

Preparation Example 5

A one-liter glass flask was charged with 804 g of deionized water and the water temperature was set to 20° C. The pH of the deionized water was measured and found to be 5.9. Next, 69.2 g of methyltrimethoxysilane was added under stirring with an anchor stirring element at a stirring speed of 150 rpm, whereupon heat generation occurred and the temperature rose to 25° C. The mixture assumed a clear state after 3 minutes and stirring was continued for another 7 minutes. Next, 85.8 g of phenyltrimethoxysilane was added and stirring was continued while keeping the temperature at 20 to 25° C., whereupon the mixture assumed a clear state after 65 minutes and stirring was continued for another 5 minutes. The mixture was then cooled to 5° C. over a period of 30 minutes. A mixed solution of 0.53 g of 28 wt % ammonia water and 2.65 g of deionized water was then poured in and the system was stirred for 30 seconds, following which stirring was stopped. Clouding arose 9 seconds after stirring was stopped.

The system was left at rest for 3 hours, following which stirring at a speed of 150 rpm was begun. The system was heated to 75° C. and 38 g of 28 wt % ammonia water was added, following which one hour of additional stirring was carried out at a temperature of 73 to 77° C. The system was then cooled to 30° C. or below, following which the liquid was removed using a press filter, leaving a filter cake. The cake was dried at a temperature of 105° C. in a circulating hot-air dryer, and the dried material was pulverized in a jet mill, giving polymethylphenylsilsesquioxane particles.

Based on the amounts of methyltrimethoxysilane and phenyltrimethoxysilane used as the starting materials, the molar ratio of methylsilsesquioxane units and phenylsilsesquioxane units in the resulting polymethylphenylsilsesquioxane particles was calculated to be 54:46.

The shapes of these polymethylphenylsilsesquioxane particles were examined under an electron microscope and found to be spherical. The volume mean size of the polymethylphenylsilsesquioxane particles was measured using an electrical sensing zone method particle size analyzer (Multisizer 3, from Beckman Coulter KK), and found to be 2.9 μm. The average refractive index, as measured by the method described above, was 1.52. The polymethylphenylsilsesquioxane particles were then dispersed to a concentration of 1 wt % in swollen, partially crosslinked methylpolysiloxane (KSG-16, from Shin-Etsu Chemical Co., Ltd.). Upon carrying out measurement under the conditions described above at a thickness of 500 μm, the total light transmittance was 90.2% and the haze was 94.1%.

Preparation Example 6

Comparative Product

A one-liter glass flask was charged with 824 g of deionized water and the water temperature was set to 20° C. The pH of the deionized water was measured and found to be 5.9. Next, 133 g of methyltrimethoxysilane was added under stirring with an anchor stirring element at a stirring speed of 150 rpm, whereupon heat generation occurred and the temperature rose to 24° C. The mixture assumed a clear state after 3 minutes and stirring was continued for another 90 minutes while holding the temperature at 24° C. Next, a mixed solution of 1.0 g of 28 wt % ammonia water and 5.0 g of deionized water was poured in and the system was stirred for 30 seconds, following which stirring was stopped. Clouding arose 110 seconds after stirring was stopped.

The system was left at rest for 1 hour, following which stirring at a speed of 150 rpm was begun. The system was heated to 75° C. and 37 g of 28 wt % ammonia water was added, following which one hour of additional stirring was carried out at a temperature of 73 to 77° C. The system was then cooled to 30° C. or below, following which the liquid was removed using a press filter, leaving a filter cake. The cake was dried at a temperature of 105° C. in a circulating hot-air dryer, and the dried material was pulverized in a jet mill, giving polymethylsilsesquioxane particles.

The shapes of these polymethylsilsesquioxane particles were examined under an electron microscope and found to be spherical. The volume mean size of the polymethylsilsesquioxane particles was measured using an electrical sensing zone method particle size analyzer (Multisizer 3, from Beckman Coulter KK), and found to be 2.1 μm. The average refractive index, as measured by the method described above, was 1.43. The polymethylsilsesquioxane particles were then dispersed to a concentration of 1 wt % in swollen, partially crosslinked methylpolysiloxane (KSG-16, from Shin-Etsu Chemical Co., Ltd.). Upon carrying out measurement under the conditions described above at a thickness of 500 μm, the total light transmittance was 92.8% and the haze was 27%.

Examples 1 to 3, Comparative Example 1 to 10

The ingredients shown in Tables 1 and 2 were mixed in a dispersion mixer, thereby producing a nonaqueous makeup base (skin texture-correcting cosmetic), and the evaluations described below were carried out. The results are presented in the tables.

TABLE 1

| Composition (wt %) | Example 1 | Example 2 | Example 3 | Comparative Example 1 | Comparative Example 2 | Comparative Example 3 | Comparative Example 4 |
|---|---|---|---|---|---|---|---|
| (C) Partially crosslinked dimethylpolysiloxane dimethicone mixture[1] | 90 | | | 95 | 90 | 70 | 90 |
| (C) Phenyl-modified, partially crosslinked dimethylpolysiloxane dimethicone mixture[2] | | 90 | | | | | |
| (D) Silicone resin-coated silicone rubber power[3] | | | 20 | | | | |
| (A) Polymethylphenylsilsesquioxane particles from Preparation Example 1 | 5 | 5 | 5 | | | | |
| Polymethylsilsesquioxane particles from Preparation Example 6 | | | | | 5 | 20 | |
| Silicone-treated titanium oxide[4] | | | | | | | 5 |
| (B) Dimethylpolysiloxane (6 cs) | 5 | | 75 | 5 | 5 | 10 | 5 |
| (B) Diphenylsiloxane phenyl trimethicone[5] | | 5 | | | | | |
| Total | 100 | 100 | 100 | 100 | 100 | 100 | 100 |
| Refractive index of overall oil that is liquid at 25° C. | 1.40 | 1.50 | 1.40 | 1.40 | 1.40 | 1.40 | 1.40 |
| Oil that is liquid at 25° C. as a proportion of overall cosmetic (wt %) | 73 | 82 | 75 | 76 | 73 | 63 | 73 |
| Skin texture-correcting effect | ◎ | ○ | ◎ | XX | X | ○ | ○ |
| Transparent look | ○ | ◎ | ○ | ◎ | ○ | Δ | XX |
| Feel on use | ◎ | ◎ | ◎ | Δ | ◎ | ◎ | X |
| Ease of application | ◎ | ◎ | ◎ | Δ | ◎ | X | X |

TABLE 2

| Composition (wt %) | Comparative Example 5 | Comparative Example 6 | Comparative Example 7 | Comparative Example 8 | Comparative Example 9 | Comparative Example 10 |
|---|---|---|---|---|---|---|
| (C) Phenyl-modified, partially crosslinked dimethylpolysiloxane dimethicone mixture[2] | 95 | 90 | 70 | 90 | | |
| (A) Polymethylphenylsilsesquioxane particles from Preparation Example 1 | | | | | 5 | 25 |
| Polymethylsilsesquioxane particles from Preparation Example 6 | | 5 | 20 | | | |
| Silicone-treated titanium oxide[4] | | | | 5 | | |
| (B) Dimethylpolysiloxane (6 cs) | | | | | 95 | 75 |
| (B) Diphenylsiloxane phenyl trimethicone[5] | 5 | 5 | 10 | 5 | | |
| Total | 100 | 100 | 100 | 100 | 100 | 100 |
| Refractive index of overall oil that is liquid at 25° C. | 1.50 | 1.50 | 1.50 | 1.50 | 1.40 | 1.40 |

TABLE 2-continued

| | Comparative Example | | | | | |
|---|---|---|---|---|---|---|
| Composition (wt %) | 5 | 6 | 7 | 8 | 9 | 10 |
| Oil that is liquid at 25° C. as a proportion of overall cosmetic (wt %) | 86 | 82 | 70 | 82 | 95 | 75 |
| Skin texture-correcting effect | X | Δ | ⊚ | ○ | X | ⊚ |
| Transparent look | ⊚ | X | XX | XX | ⊚ | X |
| Feel on use | X | ⊚ | ⊚ | XX | X | X |
| Ease of application | X | ⊚ | X | XX | ⊚ | ⊚ |

The notes in Tables 1 and 2 are as follows.
1) KSG-16 (Shin-Etsu Chemical Co., Ltd.):
(dimethicone/vinyl dimethicone) crosspolymer, 25 wt %;
dimethylpolysiloxane, 75 wt %
2) KSG-18A (Shin-Etsu Chemical Co., Ltd.):
(dimethicone/phenyl vinyl dimethicone) crosspolymer, 15 wt %;
diphenylsiloxyphenyl trimethicone, 85 wt %
3) KSP-101 (Shin-Etsu Chemical Co., Ltd.)
4) Refractive index, 2.72; average particle size, 0.25 μm
5) KF-56A (Shin-Etsu Chemical Co., Ltd.)

The contents are the amounts in which the indicated products are included (the same applies below). Some of component (B) is included in the mixture formulated in component (C).

(1) Evaluation of Properties

The cosmetics in the Examples and Comparative Examples were evaluated for the skin texture-correcting effect (inconspicuousness of pores and wrinkles), transparent look (naturalness of finish), feel on use (silkiness, smoothness) and ease of application (spreadability) of the cosmetic according to the criteria shown in Table 3 by ten expert panelists. The evaluation results thus obtained were rated according to the criteria shown below based on the average values for the ten panelists. The ratings thus obtained are presented in Tables 1 and 2.

TABLE 3

| Item evaluated | Skin texture-correcting effect | Transparent look | Feel on use | Ease of application |
|---|---|---|---|---|
| 5 points | good | good | good | good |
| 4 points | somewhat good | somewhat good | somewhat good | somewhat good |
| 3 points | ordinary | ordinary | ordinary | ordinary |
| 2 points | somewhat poor | somewhat poor | somewhat poor | somewhat poor |
| 1 point | poor | poor | poor | poor |

Rating Criteria

⊚: Average score was 4.5 points or more
○: Average score was at least 3.5 points but less than 4.5 points
Δ: Average score was at least 2.5 points but less than 3.5 points
x: Average score was at least 1.5 points but less than 2.5 points
xx: Average score was less than 1.5 points As shown in Tables 1 and 2, cosmetics containing the polymethylphenylsilsesquioxane particles of the invention had a skin texture-correcting effect, transparent look, feel on use and ease of application that were all good. By contrast, cosmetics containing polymethylsilsesquioxane particles, which is a comparative product (Preparation Example 6), had a skin texture-correcting effect or a transparent look that was unsatisfactory. When an amount capable of achieving a satisfactory skin texture-correcting effect was included (Comparative Example 9), the transparent look, feel on use and ease of application were all poor and so the effects desired in this invention could not be fully achieved. In cases where both components (C) and (D) of the invention were not included, the feel on use was poor and the skin texture-correcting effect and transparent look were inadequate.

Example 4

Water-In-Oil Makeup Cream
<Preparation of Cosmetic>
A: Ingredients 1 to 9 were uniformly mixed.
B: Ingredients 10 to 14 were uniformly mixed.
C: B was added to A and emulsified, giving a water-in-oil makeup cream.

| Composition | weight (%) |
|---|---|
| 1. Alkyl-modified, partially crosslinked, polyether-modified silicone composition[1] | 2 |
| 2. Alkyl-modified, partially crosslinked dimethypolysiloxane composition[2] | 8 |
| 3. Alkyl-branched, polyether-modified silicone[3] | 2 |
| 4. Cyclopentasiloxane | 10 |
| 5. Ethylhexyl methoxycinnamate | 5 |
| 6. Diethylaminohydroxybenzoyl hexyl benzoate | 2 |
| 7. Disteardimonium hectorite | 0.6 |
| 8. Highly polymerized methylpolysiloxane composition[4] | 3 |
| 9. Polymethylphenylsilsesquioxane particles from Preparation Example 2 | 9 |
| 10. Butylene glycol | 6 |
| 11. Sodium citrate | 0.2 |
| 12. Sodium chloride | 1 |
| 13. Phenoxyethanol | 0.3 |
| 14. Purified water | balance |
| Total | 100.0 |

Refractive index of overall oil that is liquid at 25° C.: 1.44
[1] KSG-330 (Shin-Etsu Chemical Co., Ltd.)
[2] KSG-43 (Shin-Etsu Chemical Co., Ltd.)
[3] KF-6048 (Shin-Etsu Chemical Co., Ltd.)
[4] KF-9014 (Shin-Etsu Chemical Co., Ltd.)

The resulting water-in-oil makeup cream was confirmed to have an excellent skin texture-correcting effect, transparent look, feel on use and ease of application.

Example 5

Water-In-Oil Foundation
<Preparation of Cosmetic>
A: Ingredients 1 to 9 were uniformly mixed.
B: Ingredients 14 to 18 were uniformly mixed.
C: Ingredients 10 to 13 were uniformly mixed in a dispersion mixer.
D: B was added to A and emulsified, and then C was added and uniformly mixed, giving a water-in-oil foundation.

| Composition | weight (%) |
|---|---|
| 1. Partially crosslinked, polyether-modified silicone composition[1] | 3.5 |
| 2. Partially crosslinked dimethypolysiloxane composition[2] | 6 |
| 3. Silicone-branched, polyether-modified silicone[3] | 2 |
| 4. Methyl trimethicone[4] | 9 |
| 5. Distearyldimonium hectorite | 0.6 |
| 6. Acrylic-silicone graft copolymer composition[5] | 3 |
| 7. Ethyl hexyl methoxycinnamate | 5 |
| 8. Silicone resin-coated, alkyl-modified silicone rubber powder[6] | 1 |
| 9. Polymethylphenylsilsesquioxane particles from Preparation Example 2 | 2 |
| 10. Dimethylpolysiloxane (6 cs) | 4 |
| 11. Silicone-branched, polyether-modified silicone[3] | 0.2 |
| 12. Silicone-treated titanium oxide[7] | 8.5 |
| 13. Silicone-treated iron oxide[8] | 1.5 |
| 14. Ethanol | 6 |
| 15. Sodium citrate | 0.2 |
| 16. Sodium chloride | 1 |
| 17. Methylparaben | 0.15 |
| 18. Purified water | balance |
| Total | 100.0 |

[1] KSG-210 (Shin-Etsu Chemical Co., Ltd.)
[2] KSG-16 (Shin-Etsu Chemical Co., Ltd.)
[3] KF-6028 (Shin-Etsu Chemical Co., Ltd.)
[4] TMF-1.5 (Shin-Etsu Chemical Co., Ltd.)
[5] KP-549 (Shin-Etsu Chemical Co., Ltd.)
[6] KSP-441 (Shin-Etsu Chemical Co., Ltd.)
[7] KTP-09W (Shin-Etsu Chemical Co., Ltd.)
[8] KTP-09R, Y, B (Shin-Etsu Chemical Co., Ltd.)

The resulting water-in-oil foundation was confirmed to have an excellent skin texture-correcting effect, transparent look, feel on use and ease of application.

Example 6

Water-In-Oil Makeup Cream
<Preparation of Cosmetic>
A: Ingredients 1 to 6 were uniformly mixed.
B: Ingredients 9 to 13 were uniformly mixed.
C: B was added to A and emulsified, following which ingredients 7 and 8 were added, giving a water-in-oil makeup cream.

| Composition | weight (%) |
|---|---|
| 1. Partially crosslinked, polyglycerol-modified silicone composition[1] | 3.5 |
| 2. Partially crosslinked dimethypolysiloxane composition[2] | 10 |
| 3. Silicone/alkyl-branched, polyglycerol-modified silicone[3] | 2 |
| 4. Cyclopentasiloxane | 10 |
| 5. Silicone resin-coated, phenyl-modified silicone rubber powder[4] | 3 |
| 6. Polymethylphenylsilsesquioxane particles from Preparation Example 3 | 7 |
| 7. Metal soap-treated microparticulate titanium oxide dispersion[5] | 5 |
| 8. Silicone-treated microparticulate zinc oxide dispersion[6] | 10 |
| 9. Ethanol | 6 |
| 10. Sodium citrate | 0.5 |
| 11. Magnesium sulfate | 0.5 |
| 12. Methylparaben | 0.15 |
| 13. Purified water | balance |
| Total | 100.0 |

[1] KSG-710 (Shin-Etsu Chemical Co., Ltd.)
[2] KSG-16 (Shin-Etsu Chemical Co., Ltd.)
[3] KF-6105 (Shin-Etsu Chemical Co., Ltd.)
[4] KSP-300 (Shin-Etsu Chemical Co., Ltd.)
[5] SPD-T5 (Shin-Etsu Chemical Co., Ltd.)
[6] SPD-Z5 (Shin-Etsu Chemical Co., Ltd.)

The resulting water-in-oil makeup cream was confirmed to have an excellent skin texture-correcting effect, transparent look, feel on use and ease of application.

Example 7

Mousse Concealer
<Preparation of Cosmetic>
A: Ingredients 6 to 11 were uniformly mixed on a three-roll mill.
B: A and ingredients 1 to 5 were uniformly mixed, giving a mousse concealer.

| Composition | weight (%) |
|---|---|
| 1. Silicone/alkyl co-modified, partially crosslinked dimethylpolysiloxane composition[1] | 35 |
| 2. Trimethylsiloxysilicate composition[2] | 10 |
| 3. Polymethyl methacrylate | 2 |
| 4. Silicone resin-coated silicone rubber powder[3] | 12 |
| 5. Polymethylphenylsilsesquioxane particles from Preparation Example 2 | 4 |
| 6. Dimethylpolysiloxane (6 cs) | 15 |
| 7. Metal soap-treated microparticulate titanium oxide | 9 |
| 8. Silicone-treated titanium oxide[4] | 6 |
| 9. Silicone-treated iron oxide[4] | 1 |
| 10. Silicone-treated mica[4] | 1 |
| 11. Silicone-treated talc[4] | balance |
| Total | 100.0 |

Refractive index of overall oil that is liquid at 25° C.: 1.40
[1] KSG-045Z (Shin-Etsu Chemical Co., Ltd.)
[2] KF-9021 (Shin-Etsu Chemical Co., Ltd.)
[3] KSP-100 (Shin-Etsu Chemical Co., Ltd.)
[4] Powder was subjected to hydrophobizing surface treatment using KF-9901 (Shin-Etsu Chemical Co., Ltd.)

The resulting mousse concealer was confirmed to have an excellent skin texture-correcting effect, transparent look, feel on use and ease of application.

Example 8

Stick Concealer
<Preparation of Cosmetic>
A: Ingredients 1 to 5 were uniformly mixed in a dispersion mixer.
B: A and ingredients 6 and 7 were uniformly mixed at 90° C., following which the mixture was filled into a stick container and then cooled, giving a stick concealer.

| Composition | weight (%) |
|---|---|
| 1. Partially crosslinked dimethylpolysiloxane composition[1] | 22 |
| 2. Silicone spherical powder composition[2] | 10 |
| 3. Polymethylsilsesquioxane[3] | 12 |
| 4. Polymethylphenylsilsesquioxane particles from Preparation Example 3 | 18 |

| Composition | weight (%) |
|---|---|
| 5. Dimethylpolysiloxane (6 cs) | 24 |
| 6. Ceresin | 10 |
| 7. Microcrystalline wax | 4 |
| Total | 100.0 |

Refractive index of overall oil that is liquid at 25° C.: 1.40
[1] KSG-19 (Shin-Etsu Chemical Co., Ltd.)
[2] KSG-016F (Shin-Etsu Chemical Co., Ltd.)
[3] KMP-590 (Shin-Etsu Chemical Co., Ltd.)

The resulting stick concealer was confirmed to have an excellent skin texture-correcting effect, transparent look, feel on use and ease of application.

Example 9

Cushion Foundation
<Preparation of Cosmetic>
A: Ingredients 5 to 8 were uniformly mixed on a three-roll mill.
B: A and ingredients 1 to 4 and 9 were uniformly mixed with a kneader, giving a cushion foundation.

| Composition | weight (%) |
|---|---|
| 1. Partially crosslinked dimethylpolysiloxane composition[1] | 20 |
| 2. Silicone resin-coated silicone rubber powder[2] | 1.5 |
| 3. Polymethylphenylsilsesquioxane particles from Preparation Example 4 | 8 |
| 4. Ethyl hexyl methoxycinnamate | 2 |
| 5. Acrylic-silicone graft copolymer composition[3] | 0.1 |
| 6. Triethylhexanoin | 6 |
| 7. Silicone-treated titanium oxide[4] | 20 |
| 8. Silicone-treated iron oxide[4] | 4 |
| 9. Silicone-treated talc[4] | balance |
| Total | 100.0 |

[1] KSG-16 (Shin-Etsu Chemical Co., Ltd.)
[2] KSP-100 (Shin-Etsu Chemical Co., Ltd.)
[3] KP-578 (Shin-Etsu Chemical Co., Ltd.)
[4] Powder was subjected to hydrophobizing surface treatment using KP-574 (Shin-Etsu Chemical Co., Ltd.)

The resulting cushion foundation was confirmed to have an excellent skin texture-correcting effect, transparent look, feel on use and ease of application.

Example 10

Gel Eye Color
<Preparation of Cosmetic>
A: Ingredients 1 to 3 were uniformly mixed at 80° C.
B: A and ingredients 4 and 5 were uniformly mixed at 60° C.
C: B and ingredients 6 to 11 were uniformly mixed, giving a gel eye color.

| Composition | weight (%) |
|---|---|
| 1. Isotridecyl isononanoate | 24 |
| 2. Squalane | 19.9 |
| 3. Dextrin palmitate[1] | 10 |
| 4. Partially crosslinked dimethylpolysiloxane composition[2] | 12 |
| 5. Hydrophobic anhydrous silica[3] | 0.1 |
| 6. Silicone resin-coated silicone rubber powder[4] | 8 |
| 7. Polymethylphenylsilsesquioxane particles from Preparation Example 4 | 2 |
| 8. Barium sulfate | 5 |
| 9. Alkylsilane-treated synthetic mica[5] | 13 |
| 10. Glass powder | 7 |
| 11. (PET/Al) laminate | 4.5 |
| Total | 100.0 |

[1] Rheopearl KL-2 (Chiba Flour Milling Co., Ltd.)
[2] KSG-16 (Shin-Etsu Chemical Co., Ltd.)
[3] AEROSIL R972 (Nippon Aerosil Co., Ltd.)
[4] KSP-100 (Shin-Etsu Chemical Co., Ltd.)
[5] Powder was subjected to hydrophobizing surface treatment using AES-3083 (Shin-Etsu Chemical Co., Ltd.)

The resulting gel eye color was confirmed to have an excellent skin texture-correcting effect, transparent look, feel on use and ease of application.

Example 11

Lip and Tuck
<Preparation of Cosmetic>
A: Ingredients 1 to 5 were uniformly mixed.
B: Ingredients 8 to 12 were uniformly mixed on a three-roll mill.
C: A, B and ingredients 6 and 7 were uniformly mixed, giving a lip and tuck.

| Composition | weight (%) |
|---|---|
| 1. Partially crosslinked dimethylpolysiloxane composition[1] | 25 |
| 2. Partially crosslinked dimethylpolysiloxane composition[2] | 20 |
| 3. Dimethylpolysiloxane (6 cs) | balance |
| 4. Silicone-branched, polyether-modified silicone[3] | 0.6 |
| 5. Distearyldimonium hectorite | 0.6 |
| 6. Silicone resin-coated silicone rubber powder[4] | 10 |
| 7. Polymethylphenylsilsesquioxane particles from Preparation Example 5 | 5 |
| 8. Polyglyceryl-2 triisostearate | 3 |
| 9. Mica | 1.4 |
| 10. Red No. 202 | 3 |
| 11. Yellow No. 4 | 1 |
| 12. Red No. 201 | 0.3 |
| Total | 100.0 |

[1] KSG-19 (Shin-Etsu Chemical Co., Ltd.)
[2] KSG-16 (Shin-Etsu Chemical Co., Ltd.)
[3] KF-6028 (Shin-Etsu Chemical Co., Ltd.)
[4] KSP-101 (Shin-Etsu Chemical Co., Ltd.)

The resulting lip and tuck was confirmed to have an excellent skin texture-correcting effect, transparent look, feel on use and ease of application.

Example 12

Oil-In-Water Makeup Cream
<Preparation of Cosmetic>
A: Ingredients 3 to 10 were uniformly mixed.
B: Ingredients 1 and 2 were uniformly mixed.
C: B was added to A and emulsified, giving an oil-in-water makeup cream.

| | Composition | weight (%) |
|---|---|---|
| 1. | Alkyl-modified, partially crosslinked dimethylpolysiloxane composition[1] | 0.3 |
| 2. | Polymethylphenylsilsesquioxane particles from Preparation Example 5 | 10 |
| 3. | Polysorbate-60 | 2 |
| 4. | Sodium acrylate/sodium acryloyldimethyl taurate copolymer composition[2] | 1 |
| 5. | (Ammonium acryloyldimethyl taurate/VP) | 15 |
| 6. | Butylene glycol | 10 |
| 7. | Glycerin | 3 |
| 8. | Pentylene glycol | 1 |
| 9. | Methylparaben | 0.15 |
| 10. | Purified water | balance |
| | Total | 100.0 |

[1] KSG-43 (Shin-Etsu Chemical Co., Ltd.)
[2] Simulgel EG (SEPPIC)

The resulting oil-in-water makeup cream was confirmed to have an excellent skin texture-correcting effect, transparent look, feel on use and ease of application.

Example 13

Gel Beauty Lotion
<Preparation of Cosmetic>
  A: Ingredients 5 to 10 were uniformly mixed.
  B: Ingredients 1 to 4 were uniformly mixed.
  C: B was added to A and emulsified, giving a gel beauty lotion.

| | Composition | weight (%) |
|---|---|---|
| 1. | Polyether-modified silicone[1] | 1.5 |
| 2. | Polymethylphenylsilsesquioxane particles from Preparation Example 1 | 5 |
| 3. | Silicone resin-coated silicone rubber powder[2] | 5 |
| 4. | Dimethylpolysiloxane (6 cs) | 5 |
| 5. | Carbomer | 0.2 |
| 6. | Ethanol | 8 |
| 7. | Methyl gluceth-10 | 3 |
| 8. | Bisabolol | 0.2 |
| 9. | Arginine, 10% aqueous solution | q.s. |
| 10. | Purified water | balance |
| | Total | 100.0 |

[1] KF-6011 (Shin-Etsu Chemical Co., Ltd.)
[2] KSP-101 (Shin-Etsu Chemical Co., Ltd.)

The resulting gel beauty lotion was confirmed to have an excellent skin texture-correcting effect, transparent look, feel on use and ease of application.

Example 14

Water-in-Oil Eye Cream
<Preparation of Cosmetic>
  A: Ingredients 1 to 7 were uniformly mixed at 50° C.
  B: Ingredients 8 to 12 were uniformly mixed at 50° C.
  C: B was added to A and emulsified, giving a water-in-oil eye cream.

| | Composition | weight (%) |
|---|---|---|
| 1. | Silicone/alkyl-branched, polyether-modified silicone[1] | 3.5 |
| 2. | Phenyl-modified, partially crosslinked dimethylpolysiloxane composition[2] | 5 |
| 3. | Petrolatum | 7 |
| 4. | Dimethicone (6 cs) | 10 |
| 5. | Distearyldimonium hectorite | 1.5 |
| 6. | Silicone-modified pullulan[3] | 0.5 |
| 7. | Polymethylphenylsilsesquioxane particles from Preparation Example 1 | 3 |
| 8. | Glycerin | 6 |
| 9. | Pentylene glycol | 1.5 |
| 10. | Sodium chloride | 1 |
| 11. | Phenoxyethanol | 0.3 |
| 12. | Purified water | balance |
| | Total | 100.0 |

[1] KF-6038 (Shin-Etsu Chemical Co., Ltd.)
[2] KSG-18A (Shin-Etsu Chemical Co., Ltd.)
[3] TSPL-30-D5 (Shin-Etsu Chemical Co., Ltd.)

The resulting water-in-oil eye cream was confirmed to have an excellent skin texture-correcting effect, transparent look, feel on use and ease of application.

Example 15

Lipstick
<Preparation of Cosmetic>
  A: Ingredients 1 to 13 were uniformly mixed at 95° C.
  B: Ingredients 14 to 19 were uniformly mixed on a three-roll mill.
  C: B was added to A and uniformly mixed at 85° C., following which the mixture was poured into a mold and then cooled, giving a lipstick.

| | Composition | weight (%) |
|---|---|---|
| 1. | Candelilla wax | 3.4 |
| 2. | Polyethylene | 1.6 |
| 3. | Microcrystalline wax | 2.5 |
| 4. | Ceresin | 6 |
| 5. | Silicone wax[1] | 12 |
| 6. | Silicone/alkyl branched, polyglycerol-modified silicone[2] | 2.5 |
| 7. | Pentaerythritol tetraisostearate | 10 |
| 8. | Diisostearyl malate | 8 |
| 9. | Hydrogenated polyisobutene | 8 |
| 10. | Isotridecyl isononanoate | 5 |
| 11. | Diphenyl dimethicone[3] | balance |
| 12. | Silicone resin-coated, phenyl-modified silicone rubber powder[4] | 2 |
| 13. | Polymethylphenylsilsesquioxane particles from Preparation Example 3 | 5 |
| 14. | Polyglyceryl-2 triisostearate | 5.5 |
| 15. | Mica | 1.4 |
| 16. | Red No. 202 | 0.4 |
| 17. | Yellow No. 4 | 1.4 |
| 18. | Red No. 201 | 0.3 |
| 19. | Titanium oxide | 4 |
| | Total | 100.0 |

Refractive index of overall oil that is liquid at 25° C.: 1.48
[1] KP-561P (Shin-Etsu Chemical Co., Ltd.)
[1] KF-6105 (Shin-Etsu Chemical Co., Ltd.)
[3] KF-54 (Shin-Etsu Chemical Co., Ltd.)
[3] KSP-300 (Shin-Etsu Chemical Co., Ltd.)

The resulting lipstick was confirmed to have an excellent transparent look, feel on use and ease of application. Because the refractive index of the oil is suitable, a composition having transparency without a loss of luster can be obtained.

Example 16

Sunscreen Gel

<Preparation of Cosmetic>

A: Ingredients 1 to 10 were uniformly mixed, giving a sunscreen gel.

| | Composition | weight (%) |
|---|---|---|
| 1. | Alkyl-modified, partially crosslinked dimethylpolysiloxane composition[1] | 10 |
| 2. | Phenyl-modified, partially crosslinked dimethylpolysiloxane composition[2] | 25 |
| 3. | Silicone/alkyl-modified, partially crosslinked dimethylpolysiloxane composition[3] | balance |
| 4. | Ethylhexyl methoxycinnamate | 7.5 |
| 5. | Octocrylene | 10 |
| 6. | Homosalate | 10 |
| 7. | Ethylhexyl salicylate | 5 |
| 8. | t-Butylmethoxydibenzoylmethane | 3 |
| 9. | Silicone resin-coated, phenyl-modified silicone rubber powder[4] | 10 |
| 10. | Polymethylphenylsilsesquioxane particles of Preparation Example 1 | 4 |
| | Total | 100.0 |

Refractive index of overall oil that is liquid at 25° C.: 1.49
[1] KSG-42A (Shin-Etsu Chemical Co., Ltd.)
[2] KSG-18A (Shin-Etsu Chemical Co., Ltd.)
[3] KSG-042Z (Shin-Etsu Chemical Co., Ltd.)
[4] KSP-300 (Shin-Etsu Chemical Co., Ltd.)

The resulting sunscreen gel was confirmed to have an excellent skin texture-correcting effect, transparent look, feel on use and ease of application. Also, because the refractive index of the oils is suitable, a composition having a high transparency can be obtained.

Example 17

Sunscreen Gel

<Preparation of Cosmetic>

A: Ingredients 1 to 8 were uniformly mixed, giving a sunscreen gel.

| | Composition | weight (%) |
|---|---|---|
| 1. | Modified, partially crosslinked dimethylpolysiloxane composition[1] | balance |
| 2. | Phenyl-modified, partially crosslinked dimethylpolysiloxane composition[2] | 40 |
| 3. | Ethylhexyl methoxycinnamate | 7.5 |
| 4. | Octocrylene | 3 |
| 5. | Tocopherol | 0.1 |
| 6. | Diethylaminohydroxybenzoyl hexyl benzoate | 1.5 |
| 7. | Silicone resin-coated, alkyl-modified silicone rubber powder[3] | 12 |
| 8. | Polymethylphenylsilsesquioxane particles from Preparation Example 2 | 4 |
| | Total | 100.0 |

Refractive index of overall oil that is liquid at 25° C.: 1.46
[1] KSG-15 (Shin-Etsu Chemical Co., Ltd.)
[2] KSG-18A (Shin-Etsu Chemical Co., Ltd.)
[3] KSG-441 (Shin-Etsu Chemical Co., Ltd.)

The resulting sunscreen gel was confirmed to have an excellent skin texture-correcting effect, transparent look, feel on use and ease of application. Also, because the refractive index of the oil is suitable, a composition having a high transparency can be obtained.

Example 18

Nonaqueous Sunscreen

<Preparation of Cosmetic>

A: Ingredients 1 to 5 were uniformly mixed and dissolved.

B: Ingredients 6 to 9 were uniformly mixed.

C: A and B were uniformly mixed, giving a nonaqueous sunscreen.

| | Composition | weight (%) |
|---|---|---|
| 1. | Cyclopentasiloxane | balance |
| 2. | Ethylhexyl methoxycinnamate | 7.5 |
| 3. | Ethylhexyl salicylate | 5 |
| 4. | Stearyl glycyrrhetinate | 0.2 |
| 5. | BHT | 0.1 |
| 6. | Alkyl-modified, partially crosslinked, polyglycerol-modified silicone composition[1] | 5 |
| 7. | Phenyl-modified, partially crosslinked dimethylpolysiloxane composition[2] | 45 |
| 8. | Microparticulate zinc oxide dispersion[3] | 30 |
| 9. | Polymethylphenylsilsesquioxane particles from Preparation Example 3 | 4 |
| | Total | 100.0 |

Refractive index of overall oil that is liquid at 25° C.: 1.48
[1] KSG-820 (Shin-Etsu Chemical Co., Ltd.)
[2] KSG-18A (Shin-Etsu Chemical Co., Ltd.)
[3] SPD-Z6 (Shin-Etsu Chemical Co., Ltd.)

The resulting nonaqueous sunscreen was confirmed to have an excellent skin texture-correcting effect, transparent look, feel on use and ease of application.

Example 19

Nonaqueous Sunscreen

<Preparation of Cosmetic>

A: Ingredients 1 to 5 were uniformly mixed and dissolved.

B: Ingredients 6 to 9 were uniformly mixed.

C: A and B were uniformly mixed, giving a nonaqueous sunscreen.

| | Composition | weight (%) |
|---|---|---|
| 1. | Methyl trimethicone | balance |
| 2. | Polysilicone-15 | 5 |
| 3. | Dicaprylyl carbonate | 15 |
| 4. | Stearyl glycyrrhetinate | 0.2 |
| 5. | BHT | 0.1 |
| 6. | Alkyl-modified, partially crosslinked, polyether-modified silicone composition[1] | 50 |
| 7. | Microparticulate titanium oxide dispersion[2] | 10 |
| 8. | Microparticulate zinc oxide dispersion[3] | 10 |
| 9. | Polymethylphenylsilsesquioxane particles from Preparation Example 4 | 4 |
| | Total | 100.0 |

Refractive index of overall oil that is liquid at 25° C.: 1.44
[1] KSG-330 (Shin-Etsu Chemical Co., Ltd.)
[2] SPD-T5L (Shin-Etsu Chemical Co., Ltd.)
[3] SPD-Z5L (Shin-Etsu Chemical Co., Ltd.)

The resulting nonaqueous sunscreen was confirmed to have an excellent skin texture-correcting effect, transparent look, feel on use and ease of application.

Example 20

Nonaqueous Sunscreen

<Preparation of Cosmetic>

A: Ingredients 1 to 5 were uniformly mixed and dissolved.
B: Ingredients 6 to 9 were uniformly mixed.
C: A and B were uniformly mixed, giving a nonaqueous sunscreen.

| | Composition | weight (%) |
|---|---|---|
| 1. | Diisopropyl sebacate | balance |
| 2. | Ethylhexyl methoxycinnamate | 7.5 |
| 3. | Bis-ethylhexyloxyphenol methoxyphenyl triazine | 1 |
| 4. | Stearyl glycyrrhetinate | 0.2 |
| 5. | BHT | 0.1 |
| 6. | Partially crosslinked dimethylpolysiloxane composition[1] | 40 |
| 7. | Phenyl-modified, partially crosslinked dimethylpolysiloxane composition[2] | 10 |
| 8. | Microparticulate titanium oxide dispersion[3] | 30 |
| 9. | Polymethylphenylsilsesquioxane particles from Preparation Example 1 | 4 |
| | Total | 100.0 |

Refractive index of overall oil that is liquid at 25° C.: 1.46
[1] KSG-15 (Shin-Etsu Chemical Co., Ltd.)
[2] KSG-18A (Shin-Etsu Chemical Co., Ltd.)
[3] SPD-T7 (Shin-Etsu Chemical Co., Ltd.)

The resulting nonaqueous sunscreen was confirmed to have an excellent skin texture-correcting effect, transparent look, feel on use and ease of application.

Example 21

Nonaqueous Makeup Base

<Preparation of Cosmetic>

A: Ingredients 1 to 7 were uniformly mixed.
B: Ingredients 8 to 10 were uniformly mixed on a three-roll mill.
C: A and B were uniformly mixed, giving a nonaqueous makeup base.

| | Composition | weight (%) |
|---|---|---|
| 1. | Partially crosslinked, polyether-modified silicone composition[1] | 5 |
| 2. | Partially crosslinked dimethylpolysiloxane composition[2] | 20 |
| 3. | Silicone/alkyl-modified, partially crosslinked dimethylpolysiloxane composition[3] | 15 |
| 4. | Cyclopentasiloxane | balance |
| 5. | Microparticulate titanium oxide dispersion[4] | 20 |
| 6. | Microparticulate zinc oxide dispersion[5] | 20 |
| 7. | Polymethylphenylsilsesquioxane particles from Preparation Example 5 | 4 |
| 8. | Neopentyl glycol diethylhexanoate | 0.5 |
| 9. | Silicone-treated titanium oxide[6] | 1 |
| 10 | Silicone-treated iron oxide[7] | 0.2 |
| | Total | 100.0 |

Refractive index of overall oil that is liquid at 25° C.: 1.40
[1] KSG-240 (Shin-Etsu Chemical Co., Ltd.)
[2] KSG-15 (Shin-Etsu Chemical Co., Ltd.)
[3] KSG-045Z (Shin-Etsu Chemical Co., Ltd.)
[4] SPD-T7 (Shin-Etsu Chemical Co., Ltd.)
[5] SPD-Z5 (Shin-Etsu Chemical Co., Ltd.)
[6] KTP-09W (Shin-Etsu Chemical Co., Ltd.)
[7] KTP-09R, Y, B (Shin-Etsu Chemical Co., Ltd.)

The resulting nonaqueous makeup base was confirmed to have an excellent skin texture-correcting effect, transparent look, feel on use and ease of application.

Example 22

Concealer

<Preparation of Cosmetic>

A: Ingredients 1 to 6 were uniformly mixed.
B: Ingredients 7 to 9 were uniformly mixed on a three-roll mill.
C: A and B were uniformly mixed, giving a concealer.

| | Composition | weight (%) |
|---|---|---|
| 1. | Partially crosslinked dimethylpolysiloxane composition[1] | 6 |
| 2. | Diphenylsiloxy phenyl trimethicone[2] | 7 |
| 3. | Dimethylpolysiloxane (6 cs) | balance |
| 4. | Silicone-branched, polyether-modified silicone[3] | 0.5 |
| 5. | Silicone resin-coated silicone rubber powder[4] | 25 |
| 6. | Polymethylphenylsilsesquioxane particles from Preparation Example 1 | 4 |
| 7. | Triethylhexanoin | 0.2 |
| 8. | Silicone-treated titanium oxide[5] | 0.2 |
| 9. | Silicone-treated iron oxide[6] | 0.1 |
| | Total | 100.0 |

Refractive index of overall oil that is liquid at 25° C.: 1.41
[1] KSG-19 (Shin-Etsu Chemical Co., Ltd.)
[2] KF-56A (Shin-Etsu Chemical Co., Ltd.)
[3] KF-6028 (Shin-Etsu Chemical Co., Ltd.)
[4] KSP-101 (Shin-Etsu Chemical Co., Ltd.)
[5] KTP-09W (Shin-Etsu Chemical Co., Ltd.)
[6] KTP-09R, Y, B (Shin-Etsu Chemical Co., Ltd.)

The resulting concealer was confirmed to have an excellent skin texture-correcting effect, transparent look, feel on use and ease of application.

Example 23

After Bath Treatment

<Preparation of Cosmetic>

A: Ingredients 1 to 5 were uniformly mixed.
B: Ingredients 6 to 10 were uniformly mixed.
C: B was added to A and emulsified.
D: Ingredients 11 and 12 were added to C and uniformly mixed, giving an after bath treatment.

| | Composition | weight (%) |
|---|---|---|
| 1. | Partially crosslinked, polyether-modified silicone composition[1] | 3 |
| 2. | Partially crosslinked dimethylpolysiloxane composition[2] | 1 |
| 3. | Polyether-modified silicone[3] | 0.2 |
| 4. | Polymethylphenylsilsesquioxane particles from Preparation Example 1 | 2 |
| 5. | Dimethylpolysiloxane (6 cs) | 9.8 |
| 6. | BG | 5 |
| 7. | Ethanol | 8 |
| 8. | Sodium citrate | 0.2 |
| 9. | Sodium chloride | 1 |
| 10. | Purified water | balance |

-continued

| | Composition | weight (%) |
|---|---|---|
| 11. | Polyaminopropyl biguanide, 20% aqueous solution | 0.2 |
| 12. | Fragrance | q.s. |
| | Total | 100.0 |

[1] KSG-210 (Shin-Etsu Chemical Co., Ltd.)
[2] KSG-16 (Shin-Etsu Chemical Co., Ltd.)
[3] KF-6017 (Shin-Etsu Chemical Co., Ltd.)

The resulting after bath treatment was confirmed to have a transparent look, feel on use and ease of application that are excellent.

Example 24

Hair Oil
<Preparation of Cosmetic>
A: Ingredients 1 to 8 were uniformly mixed, giving a hair oil.

| | Composition | weight (%) |
|---|---|---|
| 1. | Polymethylphenylsilsesquioxane particles from Preparation Example 2 | 2 |
| 2. | Partially crosslinked, polyglycerol-modified silicone composition[1] | 10 |
| 3. | Methyl trimethicone[2] | 35 |
| 4. | Diphenylsiloxy phenyl trimethicone[3] | 10 |
| 5. | Jojoba oil | 5 |
| 6. | Tocopherol | 0.1 |
| 7. | Isododecane | balance |
| 8. | Fragrance | q.s. |
| | Total | 100.0 |

[1] KSG-710 (Shin-Etsu Chemical Co., Ltd.)
[2] TMF-1.5 (Shin-Etsu Chemical Co., Ltd.)
[3] KF-56A (Shin-Etsu Chemical Co., Ltd.)

The resulting hair oil was confirmed to have a transparent look, feel on use and ease of application that are excellent.

Example 25

Sunscreen Stick
<Preparation of Cosmetic>
A: Ingredients 1 and 2 were heated and dissolved, following which ingredient 3 was added and uniformly mixed at 85° C.
B: Ingredients 4 to 14 were added to A and uniformly mixed at 85° C., following which the mixture was cast into a stick container, giving a sunscreen stick.

| | Composition | weight (%) |
|---|---|---|
| 1. | Dibutyl lauroyl glutamide | 2.5 |
| 2. | Hydroxystearic acid | 10 |
| 3. | Diphenylsiloxy phenyl trimethicone[1] | balance |
| 4. | Phenyl-modified, partially crosslinked dimethylpolysiloxane composition[2] | 25 |
| 5. | Mineral oil | 5 |
| 6. | Isononyl isononanoate | 15 |
| 7. | Ethylhexyl methoxycinnamate | 5 |
| 8. | Octocrylene | 5 |
| 9. | Homosalate | 8 |
| 10. | Bis-ethylhexyloxyphenol methoxyphenyl triazine | 1 |
| 11. | t-Butyl methoxydibenzoylmethane | 2.5 |
| 12. | Diethylamino hydroxybenzoyl hexyl benzoate | 2.5 |
| 13. | Polymethylphenylsilsesquioxane particles from Preparation Example 1 | 4 |
| 14. | BHT | 0.1 |
| | Total | 100.0 |

Refractive index of overall oil that is liquid at 25° C.: 1.49
[1] KF-56 (Shin-Etsu Chemical Co., Ltd.)
[2] KSG-18A (Shin-Etsu Chemical Co., Ltd.)

The resulting sunscreen stick was confirmed to have a transparent look, feel on use and ease of application that are excellent. Because the refractive index of the oil is suitable, a composition having a high transparency can be obtained, yet there is no sense of grittiness following application.

Example 26

Sunscreen Stick
<Preparation of Cosmetic>
A: Ingredients 1 to 3 were heated and dissolved, following which ingredient 4 was added and uniformly mixed at 85° C.
B: Ingredients 5 to 15 were added to A and uniformly mixed at 85° C., following which the mixture was cast into a stick container, giving a sunscreen stick.

| | Composition | weight (%) |
|---|---|---|
| 1. | Dibutyl lauroyl glutamide | 2.5 |
| 2. | Dibutyl ethylhexanoyl glutamide | 2 |
| 3. | Octyl dodecanol | 10 |
| 4. | Diphenylsiloxy phenyl trimethicone[1] | balance |
| 5. | Silicone resin-coated, phenyl-modified silicone rubber powder[2] | 3 |
| 6. | Isododecane | 5 |
| 7. | Acrylic-silicone graft copolymer composition[3] | 3 |
| 8. | Cetyl ethylhexanoate | 5 |
| 9. | Ethylhexyl methoxycinnamate | 7.5 |
| 10. | Octocrylene | 5 |
| 11. | Ethylhexyl salicylate | 5 |
| 12. | Bis-ethylhexyloxyphenol methoxyphenyl triazine | 3 |
| 13. | Diethylamino hydroxybenzoyl hexyl benzoate | 2.5 |
| 14. | Polymethylphenylsilsesquioxane particles from Preparation Example 2 | 3 |
| 15. | BHT | 0.1 |
| | Total | 100.0 |

Refractive index of overall oil that is liquid at 25° C.: 1.50
[1] KF-56A (Shin-Etsu Chemical Co., Ltd.)
[2] KSP-300 (Shin-Etsu Chemical Co., Ltd.)
[3] KP-550 (Shin-Etsu Chemical Co., Ltd.)

The resulting sunscreen stick was confirmed to have a transparent look, feel on use and ease of application that are excellent. Because the refractive index of the oil is suitable, a composition having a high transparency can be obtained, yet there is no sense of grittiness following application.

Example 27

Sunscreen Oil
<Preparation of Cosmetic>
A: Ingredients 1 to 6 were heated and dissolved, following which ingredients to 7 to 16 were added and uniformly mixed, giving a sunscreen oil.

| Composition | weight (%) |
|---|---|
| 1. Bis-ethylhexyloxyphenol methoxyphenyl triazine | 3 |
| 2. Diethylamino hydroxybenzoyl hexyl benzoate | 2.5 |
| 3. BHT | 0.1 |
| 4. Ethylhexyl methoxycinnamate | 7.5 |
| 5. Octocrylene | 5 |
| 6. Ethylhexyl salicylate | 5 |
| 7. Cyclopentasiloxane | balance |
| 8. Silicone-modified pullulan composition[1] | 1 |
| 9. Cetyl ethylhexanoate | 5 |
| 10. Ethylhexyl palmitate | 8 |
| 11. Diphenylsiloxy phenyl trimethicone[2] | 20 |
| 12. Glyceryl tri(caprylate/caprate) | 5 |
| 13. Propanediol di(caprylate/caprate) | 3 |
| 14. Polymethylphenylsilsesquioxane particles from Preparation Example 4 | 3 |
| 15. Silicone resin-coated, phenyl-modified silicone rubber powder[3] | 5 |
| 16. Tocopherol | 0.05 |
| Total | 100.0 |

Refractive index of overall oil that is liquid at 25° C.: 1.46
[1]TSPL-30-D5 (Shin-Etsu Chemical Co., Ltd.)
[2]KF-56A (Shin-Etsu Chemical Co., Ltd.)
[3]KSP-441 (Shin-Etsu Chemical Co., Ltd.)

The resulting sunscreen oil was confirmed to have a transparent look, feel on use and ease of application that are excellent. Because the refractive index of the oil is suitable, a composition having a high transparency can be obtained, yet there is no sense of grittiness following application.

Example 28

Mascara

<Preparation of Cosmetic>

A: Ingredients 1 to 5 were uniformly mixed at 95° C.

B: A and ingredients 6 to 13 were uniformly mixed at 85° C., giving a mascara.

| Composition | weight (%) |
|---|---|
| 1. Isododecane | balance |
| 2. Dextrin (palmitate/ethylhexanoate)[1] | 2 |
| 3. Ceresin | 5 |
| 4. Microcrystalline wax | 7 |
| 5. Synthetic wax | 2 |
| 6. Alkyl-modified, partially crosslinked dimethylpolysiloxane composition[2] | 5 |
| 7. Acrylic-silicone graft copolymer composition[3] | 12 |
| 8. Trimethylsiloxysilicate composition[4] | 3 |
| 9. Distearyldimonium hectorite | 5 |
| 10. Propylene carbonate | 2 |
| 11. Silicone-treated synthetic black iron oxide[5] | 5 |
| 12. Silicone-treated mica | 5 |
| 13. Polymethylphenylsilsesquioxane particles from Preparation Example 3 | 6 |
| Total | 100.0 |

[1]Rheopearl TT2 (Chiba Flour Milling Co., Ltd.)
[2]KSG-42A (Shin-Etsu Chemical Co., Ltd.)
[3]KP-550 (Shin-Etsu Chemical Co., Ltd.)
[4]KF-9021 (Shin-Etsu Chemical Co., Ltd.)
[5]KTP-09B (Shin-Etsu Chemical Co., Ltd.)

The resulting mascara was confirmed to have a transparent look, feel on use and ease of application that are excellent.

Example 29

Pressed Foundation

<Preparation of Cosmetic>

A: Ingredients 1 to 3 were uniformly mixed.

B: Ingredients 4 to 12 were uniformly mixed in a blender mill.

C: A was added to B and uniformly mixed, following which the mixture was filled into a mold and molded, giving a pressed foundation.

| Composition | weight (%) |
|---|---|
| 1. Ethylhexyl methoxycinnamate | 4.5 |
| 2. Diphenylsiloxy phenyl trimethicone[1] | 4 |
| 3. Sorbitan sesquiisostearate | 0.2 |
| 4. Silicone resin-coated silicone rubber powder[2] | 2 |
| 5. Silicone resin-coated, phenyl-modified silicone rubber powder[3] | 3 |
| 6. Polymethylphenylsilsesquioxane particles from Preparation Example 5 | 3.5 |
| 7. Polyethylene | 1 |
| 8. Barium sulfate | 4 |
| 9. Silicone-treated titanium oxide[4] | 9 |
| 10. Silicone-treated iron oxide[5] | 1 |
| 11. Silicone-treated mica[6] | 40 |
| 12. Silicone-treated talc[6] | balance |
| Total | 100.0 |

[1]KF-56A (Shin-Etsu Chemical Co., Ltd.)
[2]KSP-100 (Shin-Etsu Chemical Co., Ltd.)
[3]KSP-300 (Shin-Etsu Chemical Co., Ltd.)
[4]KTP-09W (Shin-Etsu Chemical Co., Ltd.)
[5]KTP-09R, Y, B (Shin-Etsu Chemical Co., Ltd.)
[6]Each was subjected to hydrophobizing treatment using KF-9909 (Shin-Etsu Chemical Co., Ltd.)

The resulting pressed foundation was confirmed to have an excellent skin texture-correcting effect, transparent look, feel on use and ease of application.

The invention claimed is:

1. A cosmetic comprising:
    (A) spherical organopolysiloxane particles which are at least 90 mol % composed of organosilsesquioxane units and have a volume mean particle size of from 0.1 to 30 μm and an average refractive index of from 1.44 to 1.57,
    (B) an oil, and
    one, two or more substances selected from (C) cross-linked silicones and (D) silicone-resin-coated silicone rubber powders;
    wherein the component (B) is liquid at 25° C. and has a refractive index of at least 1.38 to 1.57.

2. The cosmetic of claim 1, wherein the spherical organopolysiloxane particles of component (A) are spherical polymethylphenylsilsesquioxane particles consisting of units represented as $CH_3SiO_{3/2}$ and units represented as $C_6H_5SiO_{3/2}$, the molar ratio of $CH_3SiO_{3/2}$ units to $C_6H_5SiO_{3/2}$ units ($CH_3SiO_{3/2}$ units:$C_6H_5SiO_{3/2}$ units) being from 95:5 to 20:80.

3. The cosmetic of claim 2, wherein the molar ratio of $CH_3SiO_{3/2}$ units to $C_6H_5SiO_{3/2}$ units ($CH_3SiO_{3/2}$ units: $C_6H_5SiO_{3/2}$ units) is from 80:20 to 50:50.

4. The cosmetic of claim 1, wherein the spherical organopolysiloxane particles of component (A) have, as a dispersion obtained by dispersing 1 wt % of component (A) in a swollen, partially crosslinked methylpolysiloxane, a total light transmittance measured in accordance with JIS K 7631 and a haze measured in accordance with JIS K 7136 at a thickness of 500 μm that are each at least 80%.

5. The cosmetic of claim 1, wherein the component (B) has a refractive index of at least 1.38 and less than 1.44, which cosmetic is a skin texture-correcting cosmetic.

6. The cosmetic of claim 5 which is a nonaqueous composition.

7. The cosmetic of claim 1, wherein the component (B) has a refractive index that is from 1.44 to 1.57, which cosmetic is a sunscreen cosmetic.

8. The cosmetic of claim 7 which is a nonaqueous composition.

9. The cosmetic of claim 1, wherein the spherical organopolysiloxane particles of component (A) are spherical polymethylphenylsilsesquioxane particles consisting of units represented as $CH_3SiO_{3/2}$ and units represented as $C_6H_5SiO_{3/2}$, the molar ratio of $CH_3SiO_{3/2}$ units to $C_6H_5SiO_{3/2}$ units ($CH_3SiO_{3/2}$ units:$C_6H_5SiO_{3/2}$ units) being from 80:20 to 50:50, and have an average refractive index of from 1.47 to 1.52.

* * * * *